(12) United States Patent
Banik et al.

(10) Patent No.: US 8,622,894 B2
(45) Date of Patent: Jan. 7, 2014

(54) ARTICULATION JOINT

(75) Inventors: Michael S. Banik, Bolton, MA (US); Dennis R. Boulais, Danielson, CT (US); Lucien Alfred Couvillon, Jr., Concord, MA (US); Albert C. C. Chin, Newton, MA (US); Ian W. Hunter, Lincoln, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/341,191

(22) Filed: Dec. 30, 2011

(65) Prior Publication Data

US 2012/0165608 A1    Jun. 28, 2012

Related U.S. Application Data

(63) Continuation of application No. 12/111,082, filed on Apr. 28, 2008, now abandoned, which is a continuation of application No. 10/406,149, filed on Apr. 1, 2003, now abandoned.

(51) Int. Cl.
*A61B 1/00* (2006.01)

(52) U.S. Cl.
USPC ............................ 600/142; 600/139; 600/141

(58) Field of Classification Search
USPC .......................... 600/139, 141, 142, 146, 149
See application file for complete search history.

(56) References Cited

U.S. PATENT DOCUMENTS

| | | |
|---|---|---|
| 3,266,059 A | 8/1966 | Stelle |
| 3,470,876 A | 10/1969 | Barchilon |
| 3,572,325 A | 3/1971 | Bazell et al. |
| 3,581,738 A | 6/1971 | Moore |
| 4,108,211 A | 8/1978 | Tanaka |
| 4,286,585 A | 9/1981 | Ogawa |
| 4,294,162 A | 10/1981 | Fowler et al. |
| 4,311,134 A | 1/1982 | Mitsui et al. |
| 4,315,309 A | 2/1982 | Coli |
| 4,351,323 A | 9/1982 | Ouchi et al. |
| 4,425,113 A | 1/1984 | Bilstad |
| 4,432,349 A | 2/1984 | Oshiro |
| 4,471,766 A | 9/1984 | Terayama |
| 4,473,841 A | 9/1984 | Murakoshi et al. |
| 4,488,039 A | 12/1984 | Sato et al. |
| 4,491,865 A | 1/1985 | Danna et al. |
| 4,493,537 A | 1/1985 | Nakahashi |
| 4,495,134 A | 1/1985 | Ouchi et al. |
| 4,499,895 A | 2/1985 | Takayama |
| 4,503,842 A | 3/1985 | Takayama |

(Continued)

FOREIGN PATENT DOCUMENTS

| | | |
|---|---|---|
| DE | 87 14 480 | 4/1988 |
| EP | 0 075 153 | 3/1983 |

(Continued)

*Primary Examiner* — Matthew J Kasztejna
(74) *Attorney, Agent, or Firm* — Bookoff McAndrews, PLLC

(57) ABSTRACT

An endoscopic imaging system includes a reusable control cabinet having a number of actuators that control the orientation of a lightweight endoscope that is connectable thereto. The endoscope is used with a single patient and is then disposed. The endoscope includes an illumination mechanism, an image sensor and an elongate shaft having one or more lumens located therein. A polymeric articulation joint at the distal end of the endoscope allows the distal end to be oriented by the control cabinet. The endoscope is coated with a hydrophilic coating that reduces its coefficient of friction and because it is lightweight, requires less force to advance it to a desired location within a patient.

17 Claims, 28 Drawing Sheets

(56) References Cited

U.S. PATENT DOCUMENTS

| | | |
|---|---|---|
| 4,513,235 A | 4/1985 | Acklam et al. |
| 4,515,444 A | 5/1985 | Prescott et al. |
| 4,516,063 A | 5/1985 | Kaye et al. |
| 4,519,391 A | 5/1985 | Murakoshi |
| 4,552,130 A | 11/1985 | Kinoshita |
| 4,559,928 A | 12/1985 | Takayama |
| 4,566,437 A | 1/1986 | Yamaguchi |
| 4,573,450 A | 3/1986 | Arakawa |
| 4,580,210 A | 4/1986 | Nordstrom |
| 4,586,923 A | 5/1986 | Gould et al. |
| 4,615,330 A | 10/1986 | Nagasaki et al. |
| 4,616,630 A | 10/1986 | Arakawa |
| 4,617,915 A | 10/1986 | Arakawa |
| 4,618,884 A | 10/1986 | Nagasaki |
| 4,621,618 A | 11/1986 | Omagari et al. |
| 4,622,584 A | 11/1986 | Nagasaki et al. |
| 4,625,714 A | 12/1986 | Toyota |
| 4,631,582 A | 12/1986 | Nagasaki et al. |
| 4,633,303 A | 12/1986 | Nagasaki et al. |
| 4,633,304 A | 12/1986 | Nagasaki |
| 4,643,170 A | 2/1987 | Miyazaki et al. |
| 4,646,723 A | 3/1987 | Arakawa |
| 4,649,904 A | 3/1987 | Krauter et al. |
| 4,651,202 A | 3/1987 | Arakawa |
| 4,652,093 A | 3/1987 | Stephen et al. |
| 4,654,701 E | 3/1987 | Yabe |
| RE32,421 E | 5/1987 | Hattori |
| 4,662,725 A | 5/1987 | Nisioka |
| 4,663,657 A | 5/1987 | Nagasaki et al. |
| 4,667,655 A | 5/1987 | Ogiu et al. |
| 4,674,844 A | 6/1987 | Nishioka et al. |
| 4,686,963 A | 8/1987 | Cohen et al. |
| 4,697,210 A | 9/1987 | Toyota et al. |
| 4,700,693 A | 10/1987 | Lia et al. |
| 4,713,051 A | 12/1987 | Steppe et al. |
| 4,714,075 A | 12/1987 | Krauter et al. |
| 4,716,457 A | 12/1987 | Matsuo |
| 4,719,508 A | 1/1988 | Sasaki et al. |
| 4,727,417 A | 2/1988 | Kanno et al. |
| 4,727,418 A | 2/1988 | Kato et al. |
| 4,745,470 A | 5/1988 | Yabe et al. |
| 4,745,471 A | 5/1988 | Takamura et al. |
| 4,746,974 A | 5/1988 | Matsuo |
| 4,748,970 A | 6/1988 | Nakajima |
| 4,755,029 A | 7/1988 | Okobe |
| 4,758,238 A | 7/1988 | Sundblom et al. |
| 4,762,119 A | 8/1988 | Allred et al. |
| 4,765,312 A | 8/1988 | Sasa et al. |
| 4,766,489 A | 8/1988 | Kato |
| 4,787,369 A | 11/1988 | Allred et al. |
| 4,790,294 A | 12/1988 | Allred et al. |
| 4,794,913 A | 1/1989 | Shimonaka et al. |
| 4,796,607 A | 1/1989 | Allred et al. |
| 4,800,869 A | 1/1989 | Nakajima |
| 4,805,596 A | 2/1989 | Hatori |
| 4,806,011 A | 2/1989 | Bettinger |
| 4,816,909 A | 3/1989 | Kimura et al. |
| 4,819,065 A | 4/1989 | Eino |
| 4,819,077 A | 4/1989 | Kikuchi et al. |
| 4,821,116 A | 4/1989 | Nagasaki et al. |
| 4,824,225 A | 4/1989 | Nishioka |
| 4,831,437 A | 5/1989 | Nishioka et al. |
| 4,834,069 A | 5/1989 | Umeda |
| 4,836,187 A | 6/1989 | Iwakoshi et al. |
| 4,844,052 A | 7/1989 | Iwakoshi et al. |
| 4,844,071 A | 7/1989 | Chen et al. |
| 4,845,553 A | 7/1989 | Konomura et al. |
| 4,845,555 A | 7/1989 | Yabe et al. |
| 4,847,694 A | 7/1989 | Nishihara |
| 4,853,772 A | 8/1989 | Kikuchi |
| 4,860,731 A | 8/1989 | Matsuura |
| 4,867,546 A | 9/1989 | Nishioka et al. |
| 4,868,647 A | 9/1989 | Uehara et al. |
| 4,869,237 A | 9/1989 | Eino et al. |
| 4,873,965 A | 10/1989 | Danieli |
| 4,875,468 A | 10/1989 | Krauter et al. |
| 4,877,314 A | 10/1989 | Kanamori |
| 4,882,623 A | 11/1989 | Uchikubo |
| 4,884,134 A | 11/1989 | Tsuji et al. |
| 4,885,634 A | 12/1989 | Yabe |
| 4,890,159 A | 12/1989 | Ogiu |
| 4,894,715 A | 1/1990 | Uchikubo et al. |
| 4,895,431 A | 1/1990 | Tsujiuchi et al. |
| 4,897,789 A | 1/1990 | King et al. |
| 4,899,731 A | 2/1990 | Takayama et al. |
| 4,899,732 A | 2/1990 | Cohen |
| 4,899,787 A | 2/1990 | Ouchi et al. |
| 4,905,666 A | 3/1990 | Fukuda |
| 4,918,521 A | 4/1990 | Yabe et al. |
| 4,919,112 A | 4/1990 | Siegmund |
| 4,919,114 A | 4/1990 | Miyazaki |
| 4,920,980 A | 5/1990 | Jackowski |
| 4,928,172 A | 5/1990 | Uehara et al. |
| 4,930,494 A | 6/1990 | Takehana et al. |
| 4,931,867 A | 6/1990 | Kikuchi |
| 4,941,454 A | 7/1990 | Wood et al. |
| 4,941,456 A | 7/1990 | Wood et al. |
| 4,951,134 A | 8/1990 | Nakasima et al. |
| 4,951,135 A | 8/1990 | Sasagawa et al. |
| 4,952,040 A | 8/1990 | Igarashi |
| 4,959,710 A | 9/1990 | Uehara et al. |
| 4,960,127 A | 10/1990 | Noce et al. |
| 4,961,110 A | 10/1990 | Nakamura |
| 4,967,269 A | 10/1990 | Sasagawa et al. |
| 4,971,034 A | 11/1990 | Doi et al. |
| 4,973,311 A | 11/1990 | Iwakoshi et al. |
| 4,979,497 A | 12/1990 | Matsuura et al. |
| 4,982,725 A | 1/1991 | Hibino et al. |
| 4,984,878 A | 1/1991 | Miyano |
| 4,986,642 A | 1/1991 | Yokota et al. |
| 4,987,884 A | 1/1991 | Nishioka et al. |
| 4,989,075 A | 1/1991 | Ito |
| 4,989,581 A | 2/1991 | Tamburrino et al. |
| 4,996,974 A | 3/1991 | Ciarlei |
| 4,996,975 A | 3/1991 | Nakamura |
| 5,001,556 A | 3/1991 | Nakamura et al. |
| 5,005,558 A | 4/1991 | Aomori |
| 5,005,957 A | 4/1991 | Kanamori et al. |
| 5,007,408 A | 4/1991 | Ieoka |
| 5,018,509 A | 5/1991 | Suzuki et al. |
| 5,022,382 A | 6/1991 | Ohshoki et al. |
| 5,029,016 A | 7/1991 | Hiyama et al. |
| 5,034,888 A | 7/1991 | Uehara et al. |
| 5,040,069 A | 8/1991 | Matsumoto et al. |
| RE33,689 E | 9/1991 | Nishioka et al. |
| 5,045,935 A | 9/1991 | Kikuchi |
| 5,049,989 A | 9/1991 | Tsuji |
| 5,050,584 A | 9/1991 | Matsuura |
| 5,050,974 A | 9/1991 | Takasugi et al. |
| 5,056,503 A | 10/1991 | Nagasaki |
| 5,061,994 A | 10/1991 | Takahashi |
| 5,068,719 A | 11/1991 | Tsuji |
| 5,074,861 A | 12/1991 | Schneider et al. |
| 5,081,524 A | 1/1992 | Tsuruoka et al. |
| 5,087,989 A | 2/1992 | Igarashi |
| 5,110,645 A | 5/1992 | Matsumoto et al. |
| 5,111,281 A | 5/1992 | Sekiguchi |
| 5,111,306 A | 5/1992 | Kanno et al. |
| 5,111,804 A | 5/1992 | Funakoshi |
| 5,113,254 A | 5/1992 | Kanno et al. |
| 5,119,238 A | 6/1992 | Igarashi |
| 5,131,393 A | 7/1992 | Ishiguro et al. |
| 5,137,013 A | 8/1992 | Chiba et al. |
| 5,140,265 A | 8/1992 | Sakiyama et al. |
| 5,159,446 A | 10/1992 | Hibino et al. |
| 5,170,775 A | 12/1992 | Tagami |
| 5,172,225 A | 12/1992 | Takahashi et al. |
| 5,174,293 A | 12/1992 | Hagiwara |
| 5,176,629 A | 1/1993 | Kullas et al. |
| 5,191,878 A | 3/1993 | Iida et al. |
| 5,198,931 A | 3/1993 | Igarashi |
| 5,201,908 A | 4/1993 | Jones |
| 5,208,702 A | 5/1993 | Shiraiwa |
| 5,209,220 A | 5/1993 | Hiyama et al. |

(56) References Cited

U.S. PATENT DOCUMENTS

| | | |
|---|---|---|
| 5,225,958 A | 7/1993 | Nakamura |
| 5,228,356 A | 7/1993 | Chuang |
| 5,243,416 A | 9/1993 | Nakazawa |
| 5,243,967 A | 9/1993 | Hibino |
| 5,257,628 A | 11/1993 | Ishiguro et al. |
| 5,271,381 A | 12/1993 | Ailinger et al. |
| RE34,504 E | 1/1994 | Uehara et al. |
| 5,275,152 A | 1/1994 | Krauter et al. |
| 5,291,010 A | 3/1994 | Tsuji |
| 5,299,559 A | 4/1994 | Bruce et al. |
| 5,311,858 A | 5/1994 | Adair |
| 5,324,422 A | 6/1994 | Colleran et al. |
| 5,325,845 A | 7/1994 | Adair et al. |
| 5,331,551 A | 7/1994 | Tsuruoka et al. |
| 5,342,299 A | 8/1994 | Snoke et al. |
| 5,347,989 A | 9/1994 | Monroe et al. |
| 5,374,953 A | 12/1994 | Sasaki et al. |
| 5,379,757 A | 1/1995 | Hiyama et al. |
| 5,381,782 A | 1/1995 | DeLaRama et al. |
| 5,390,662 A | 2/1995 | Okada |
| 5,400,769 A | 3/1995 | Tanii et al. |
| 5,402,768 A | 4/1995 | Adair |
| 5,402,769 A | 4/1995 | Tsuji |
| 5,409,485 A | 4/1995 | Suda |
| 5,412,478 A | 5/1995 | Ishihara et al. |
| 5,418,649 A | 5/1995 | Igarashi |
| 5,420,644 A | 5/1995 | Watanabe |
| 5,431,645 A | 7/1995 | Smith et al. |
| 5,434,615 A | 7/1995 | Matumoto |
| 5,436,640 A | 7/1995 | Reeves |
| 5,436,767 A | 7/1995 | Suzuki et al. |
| 5,440,341 A | 8/1995 | Suzuki et al. |
| 5,448,989 A | 9/1995 | Heckele |
| 5,464,007 A | 11/1995 | Krauter et al. |
| 5,469,840 A | 11/1995 | Tanii et al. |
| 5,473,235 A | 12/1995 | Lance et al. |
| 5,482,029 A | 1/1996 | Sekiguchi et al. |
| 5,483,951 A | 1/1996 | Frassica et al. |
| 5,484,407 A | 1/1996 | Osypka |
| 5,485,316 A | 1/1996 | Mori et al. |
| 5,496,260 A | 3/1996 | Krauter et al. |
| 5,515,449 A | 5/1996 | Tsuruoka et al. |
| 5,518,501 A | 5/1996 | Oneda et al. |
| 5,518,502 A | 5/1996 | Kaplan et al. |
| 5,543,831 A | 8/1996 | Tsuji et al. |
| 5,569,158 A | 10/1996 | Suzuki et al. |
| 5,569,159 A | 10/1996 | Anderson et al. |
| 5,586,262 A | 12/1996 | Komatsu et al. |
| 5,589,854 A | 12/1996 | Tsai |
| 5,591,202 A | 1/1997 | Slater et al. |
| 5,608,451 A | 3/1997 | Konno et al. |
| 5,609,561 A | 3/1997 | Uehara et al. |
| 5,619,380 A | 4/1997 | Agasawa et al. |
| 5,622,528 A | 4/1997 | Hamano et al. |
| 5,631,695 A | 5/1997 | Nakamura et al. |
| 5,633,203 A | 5/1997 | Adair |
| 5,643,203 A | 7/1997 | Beiser et al. |
| 5,645,075 A | 7/1997 | Palmer et al. |
| 5,647,840 A | 7/1997 | D'Amelio et al. |
| 5,658,238 A | 8/1997 | Suzuki et al. |
| 5,667,477 A | 9/1997 | Segawa |
| 5,674,182 A | 10/1997 | Suzuki et al. |
| 5,674,197 A | 10/1997 | van Muiden et al. |
| 5,679,216 A | 10/1997 | Takayama et al. |
| 5,685,823 A | 11/1997 | Ito et al. |
| 5,685,825 A | 11/1997 | Takase et al. |
| 5,691,853 A | 11/1997 | Miyano |
| 5,695,450 A | 12/1997 | Yabe et al. |
| 5,698,866 A | 12/1997 | Doiron et al. |
| 5,702,349 A | 12/1997 | Morizumi |
| 5,702,754 A | 12/1997 | Zhong |
| 5,703,724 A | 12/1997 | Miyano |
| 5,704,371 A | 1/1998 | Shepard |
| 5,704,896 A | 1/1998 | Fukunishi et al. |
| 5,708,482 A | 1/1998 | Takahashi et al. |
| 5,721,566 A | 2/1998 | Rosenberg et al. |
| 5,724,068 A | 3/1998 | Sanchez et al. |
| 5,728,045 A | 3/1998 | Komi |
| 5,739,811 A | 4/1998 | Rosenberg et al. |
| 5,740,801 A | 4/1998 | Branson |
| 5,741,429 A | 4/1998 | Donadio et al. |
| 5,746,696 A | 5/1998 | Kondo |
| 5,749,828 A | 5/1998 | Solomon et al. |
| 5,764,809 A | 6/1998 | Nomami et al. |
| 5,767,839 A | 6/1998 | Rosenberg |
| 5,779,686 A | 7/1998 | Sato et al. |
| 5,781,172 A | 7/1998 | Engel et al. |
| 5,787,897 A | 8/1998 | Kieturakis |
| 5,788,714 A | 8/1998 | Ouchi |
| 5,789,047 A | 8/1998 | Sasaki et al. |
| 5,793,539 A | 8/1998 | Konno et al. |
| 5,805,140 A | 9/1998 | Rosenberg et al. |
| 5,810,715 A | 9/1998 | Moriyama |
| 5,812,983 A | 9/1998 | Kumagai |
| 5,819,736 A | 10/1998 | Avny et al. |
| 5,820,591 A | 10/1998 | Thompson et al. |
| 5,821,466 A | 10/1998 | Clark et al. |
| 5,821,920 A | 10/1998 | Rosenberg et al. |
| 5,823,948 A | 10/1998 | Ross, Jr. et al. |
| 5,827,186 A | 10/1998 | Chen et al. |
| 5,827,190 A | 10/1998 | Palcic et al. |
| 5,828,197 A | 10/1998 | Martin et al. |
| 5,828,363 A | 10/1998 | Yaniger et al. |
| 5,830,124 A | 11/1998 | Suzuki et al. |
| 5,830,128 A | 11/1998 | Tanaka |
| 5,836,869 A | 11/1998 | Kudo et al. |
| 5,837,003 A | 11/1998 | Ginsburg |
| 5,837,023 A | 11/1998 | Koike et al. |
| 5,840,014 A | 11/1998 | Miyano et al. |
| 5,841,126 A | 11/1998 | Fossum et al. |
| 5,843,000 A | 12/1998 | Nishioka et al. |
| 5,846,183 A | 12/1998 | Chilcoat |
| 5,855,560 A | 1/1999 | Idaomi et al. |
| 5,857,963 A | 1/1999 | Pelchy et al. |
| 5,857,964 A | 1/1999 | Konstorum et al. |
| 5,865,724 A | 2/1999 | Palmer et al. |
| 5,868,664 A | 2/1999 | Speier et al. |
| 5,868,666 A | 2/1999 | Okada et al. |
| 5,873,816 A | 2/1999 | Kagawa et al. |
| 5,873,866 A | 2/1999 | Kondo et al. |
| 5,876,326 A | 3/1999 | Takamura et al. |
| 5,876,331 A | 3/1999 | Wu et al. |
| 5,876,373 A | 3/1999 | Giba et al. |
| 5,876,427 A | 3/1999 | Chen et al. |
| 5,877,819 A | 3/1999 | Branson |
| 5,879,284 A | 3/1999 | Tsujita |
| 5,880,714 A | 3/1999 | Rosenberg et al. |
| 5,882,293 A | 3/1999 | Ouchi |
| 5,882,339 A | 3/1999 | Beiser et al. |
| 5,889,670 A | 3/1999 | Schuler et al. |
| 5,889,672 A | 3/1999 | Schuler et al. |
| 5,892,630 A | 4/1999 | Broome |
| 5,895,350 A | 4/1999 | Hori |
| 5,897,507 A | 4/1999 | Kortenbach et al. |
| 5,897,525 A | 4/1999 | Dey et al. |
| 5,907,487 A | 5/1999 | Rosenberg et al. |
| 5,916,147 A | 6/1999 | Boury |
| 5,923,018 A | 7/1999 | Kameda et al. |
| 5,928,136 A | 7/1999 | Barry |
| 5,929,607 A | 7/1999 | Rosenberg et al. |
| 5,929,846 A | 7/1999 | Rosenberg et al. |
| 5,929,900 A | 7/1999 | Yamanaka |
| 5,929,901 A | 7/1999 | Adair et al. |
| 5,931,833 A | 8/1999 | Silverstein |
| 5,933,809 A | 8/1999 | Hunt et al. |
| 5,935,085 A | 8/1999 | Welsh et al. |
| 5,936,778 A | 8/1999 | Miyano et al. |
| 5,941,817 A | 8/1999 | Crawford |
| 5,950,168 A | 9/1999 | Simborg et al. |
| 5,951,462 A | 9/1999 | Yamanaka |
| 5,956,416 A | 9/1999 | Tsuruoka et al. |
| 5,956,689 A | 9/1999 | Everhart |
| 5,956,690 A | 9/1999 | Haggerson et al. |
| 5,959,613 A | 9/1999 | Rosenberg et al. |

(56) References Cited

U.S. PATENT DOCUMENTS

| | | |
|---|---|---|
| 5,976,070 A | 11/1999 | Ono et al. |
| 5,976,074 A | 11/1999 | Moriyama |
| 5,980,454 A | 11/1999 | Broome |
| 5,980,468 A | 11/1999 | Zimmon |
| 5,986,693 A | 11/1999 | Adair et al. |
| 5,991,729 A | 11/1999 | Barry et al. |
| 5,991,730 A | 11/1999 | Lubin et al. |
| 5,999,168 A | 12/1999 | Rosenberg et al. |
| 6,002,425 A | 12/1999 | Yamanaka et al. |
| 6,007,482 A | 12/1999 | Madni et al. |
| 6,007,531 A | 12/1999 | Snoke et al. |
| 6,009,925 A | 1/2000 | Hall et al. |
| 6,014,630 A | 1/2000 | Jeacock et al. |
| 6,015,088 A | 1/2000 | Parker et al. |
| 6,017,322 A | 1/2000 | Snoke et al. |
| 6,020,875 A | 2/2000 | Moore et al. |
| 6,020,876 A | 2/2000 | Rosenberg et al. |
| 6,026,363 A | 2/2000 | Shepard |
| 6,030,360 A | 2/2000 | Biggs |
| 6,032,120 A | 2/2000 | Rock et al. |
| 6,039,728 A | 3/2000 | Berlien et al. |
| 6,043,839 A | 3/2000 | Adair et al. |
| 6,050,718 A | 4/2000 | Schena et al. |
| 6,057,828 A | 5/2000 | Rosenberg et al. |
| 6,059,719 A | 5/2000 | Yamamoto et al. |
| 6,061,004 A | 5/2000 | Rosenberg |
| 6,067,077 A | 5/2000 | Martin et al. |
| 6,071,248 A | 6/2000 | Zimmon |
| 6,075,555 A | 6/2000 | Street |
| 6,078,308 A | 6/2000 | Rosenberg et al. |
| 6,078,353 A | 6/2000 | Yamanaka et al. |
| 6,078,876 A | 6/2000 | Rosenberg et al. |
| 6,080,104 A | 6/2000 | Ozawa et al. |
| 6,081,809 A | 6/2000 | Kumagai |
| 6,083,152 A | 7/2000 | Strong |
| 6,083,170 A | 7/2000 | Ben-Haim |
| 6,095,971 A | 8/2000 | Takahashi |
| 6,099,465 A | 8/2000 | Inoue |
| 6,100,874 A | 8/2000 | Schena et al. |
| 6,104,382 A | 8/2000 | Martin et al. |
| 6,107,004 A | 8/2000 | Donadio, III |
| 6,120,435 A | 9/2000 | Eino |
| 6,125,337 A | 9/2000 | Rosenberg et al. |
| 6,128,006 A | 10/2000 | Rosenberg et al. |
| 6,132,369 A | 10/2000 | Takahashi |
| 6,134,056 A | 10/2000 | Nakamura |
| 6,134,506 A | 10/2000 | Rosenberg et al. |
| 6,135,946 A | 10/2000 | Konen et al. |
| 6,139,508 A | 10/2000 | Simpson et al. |
| 6,141,037 A | 10/2000 | Upton et al. |
| 6,142,956 A | 11/2000 | Kortenbach et al. |
| 6,146,355 A | 11/2000 | Biggs |
| 6,149,607 A | 11/2000 | Simpson et al. |
| 6,152,877 A | 11/2000 | Masters |
| 6,154,198 A | 11/2000 | Rosenberg |
| 6,154,248 A | 11/2000 | Ozawa et al. |
| 6,155,988 A | 12/2000 | Peters |
| 6,181,481 B1 | 1/2001 | Yamamoto et al. |
| 6,184,922 B1 | 2/2001 | Saito et al. |
| 6,193,714 B1 | 2/2001 | McGaffigan et al. |
| 6,195,592 B1 | 2/2001 | Schuler et al. |
| 6,203,493 B1 | 3/2001 | Ben-Haim |
| 6,206,824 B1 | 3/2001 | Ohara et al. |
| 6,210,337 B1 | 4/2001 | Dunham et al. |
| 6,211,904 B1 | 4/2001 | Adair |
| 6,216,104 B1 | 4/2001 | Moshfeghi et al. |
| 6,219,091 B1 | 4/2001 | Yamanaka et al. |
| 6,221,070 B1 | 4/2001 | Tu et al. |
| 6,238,799 B1 | 5/2001 | Opolski |
| 6,241,668 B1 | 6/2001 | Herzog |
| 6,260,994 B1 | 7/2001 | Matsumoto et al. |
| 6,270,453 B1 | 8/2001 | Sakai |
| 6,272,470 B1 | 8/2001 | Teshima |
| 6,275,255 B1 | 8/2001 | Adair et al. |
| 6,283,960 B1 | 9/2001 | Ashley |
| 6,295,082 B1 | 9/2001 | Dowdy et al. |
| 6,299,625 B1 | 10/2001 | Bacher |
| 6,309,347 B1 | 10/2001 | Takahashi et al. |
| 6,310,642 B1 | 10/2001 | Adair et al. |
| 6,319,196 B1 | 11/2001 | Minami |
| 6,319,197 B1 | 11/2001 | Tsuji et al. |
| 6,334,844 B1 | 1/2002 | Akiba |
| 6,346,075 B1 | 2/2002 | Arai et al. |
| 6,364,828 B1 | 4/2002 | Yeung et al. |
| 6,365,828 B1 | 4/2002 | Kinoshita et al. |
| 6,366,799 B1 | 4/2002 | Acker et al. |
| 6,381,029 B1 | 4/2002 | Tipirneni |
| 6,398,724 B1 | 6/2002 | May et al. |
| 6,408,889 B1 | 6/2002 | Komachi |
| 6,413,207 B1 | 7/2002 | Minami |
| 6,421,078 B1 | 7/2002 | Akai et al. |
| 6,425,535 B1 | 7/2002 | Akiba |
| 6,425,858 B1 | 7/2002 | Minami |
| 6,436,032 B1 | 8/2002 | Eto et al. |
| 6,441,845 B1 | 8/2002 | Matsumoto |
| 6,447,444 B1 | 9/2002 | Avni et al. |
| 6,449,006 B1 | 9/2002 | Shipp |
| 6,453,190 B1 | 9/2002 | Acker et al. |
| 6,454,162 B1 | 9/2002 | Teller |
| 6,459,447 B1 | 10/2002 | Okada et al. |
| 6,468,204 B2 | 10/2002 | Sendai et al. |
| 6,475,141 B2 | 11/2002 | Abe |
| 6,478,730 B1 | 11/2002 | Bala et al. |
| 6,480,389 B1 | 11/2002 | Shie et al. |
| 6,482,149 B1 | 11/2002 | Torii |
| 6,489,987 B1 | 12/2002 | Higuchi et al. |
| 6,496,737 B2 | 12/2002 | Rudie et al. |
| 6,496,827 B2 | 12/2002 | Kozam et al. |
| 6,498,948 B1 | 12/2002 | Ozawa et al. |
| 6,503,193 B1 | 1/2003 | Iwasaki et al. |
| 6,503,195 B1 | 1/2003 | Keller et al. |
| 6,511,454 B1 | 1/2003 | Nakao et al. |
| 6,520,908 B1 | 2/2003 | Ikeda et al. |
| 6,524,234 B2 | 2/2003 | Ouchi |
| 6,530,882 B1 | 3/2003 | Farkas et al. |
| 6,533,722 B2 | 3/2003 | Nakashima |
| 6,540,669 B2 | 4/2003 | Abe et al. |
| 6,544,194 B1 | 4/2003 | Kortenbach et al. |
| 6,545,703 B1 | 4/2003 | Takahashi et al. |
| 6,551,239 B2 | 4/2003 | Renner et al. |
| 6,551,240 B2 | 4/2003 | Henzler |
| 6,558,317 B2 | 5/2003 | Takahashi et al. |
| 6,561,971 B1 | 5/2003 | Akiba |
| 6,565,507 B2 | 5/2003 | Kamata et al. |
| 6,569,086 B2 | 5/2003 | Motoki et al. |
| 6,574,629 B1 | 6/2003 | Cooke, Jr. et al. |
| 6,589,162 B2 | 7/2003 | Nakashima et al. |
| 6,595,913 B2 | 7/2003 | Takahashi |
| 6,597,390 B1 | 7/2003 | Higuchi |
| 6,599,239 B2 | 7/2003 | Hayakawa et al. |
| 6,602,186 B1 | 8/2003 | Sugimoto et al. |
| 6,605,035 B2 | 8/2003 | Ando et al. |
| 6,609,135 B1 | 8/2003 | Omori et al. |
| 6,611,846 B1 | 8/2003 | Stoodley |
| 6,614,969 B2 | 9/2003 | Eichelberger et al. |
| 6,616,601 B2 | 9/2003 | Hayakawa |
| 6,623,424 B2 | 9/2003 | Hayakawa et al. |
| 6,638,214 B2 | 10/2003 | Akiba |
| 6,638,215 B2 | 10/2003 | Kobayashi |
| 6,641,528 B2 | 11/2003 | Torii |
| 6,651,669 B1 | 11/2003 | Burnside |
| 6,656,110 B1 | 12/2003 | Irion et al. |
| 6,656,112 B2 | 12/2003 | Miyanaga |
| 6,659,940 B2 | 12/2003 | Adler |
| 6,663,561 B2 | 12/2003 | Sugimoto et al. |
| 6,669,629 B2 | 12/2003 | Matsui |
| 6,673,012 B2 | 1/2004 | Fujii et al. |
| 6,677,984 B2 | 1/2004 | Kobayashi et al. |
| 6,678,397 B1 | 1/2004 | Ohmori et al. |
| 6,682,479 B1 | 1/2004 | Takahashi et al. |
| 6,682,493 B2 | 1/2004 | Mirigian |
| 6,685,631 B2 | 2/2004 | Minami |
| 6,686,949 B2 | 2/2004 | Kobayashi et al. |
| 6,690,409 B1 | 2/2004 | Takahashi |

(56) References Cited

U.S. PATENT DOCUMENTS

| | | |
|---|---|---|
| 6,690,963 B2 | 2/2004 | Ben-Haim et al. |
| 6,692,251 B1 | 2/2004 | Logan et al. |
| 6,692,431 B2 | 2/2004 | Kazakevich |
| 6,697,101 B1 | 2/2004 | Takahashi et al. |
| 6,699,181 B2 | 3/2004 | Wako |
| 6,702,737 B2 | 3/2004 | Hinto et al. |
| 6,711,426 B2 | 3/2004 | Benaron et al. |
| 6,715,068 B1 | 3/2004 | Kazunori |
| 6,716,162 B2 | 4/2004 | Hakamata |
| 6,726,675 B1 | 4/2004 | Beyar |
| 6,728,599 B2 | 4/2004 | Wang et al. |
| 6,730,018 B2 | 5/2004 | Takase |
| 6,734,893 B1 | 5/2004 | Hess et al. |
| 6,736,773 B2 | 5/2004 | Wendlandt et al. |
| 6,743,239 B1 | 6/2004 | Kuehn et al. |
| 6,743,240 B2 | 6/2004 | Smith et al. |
| 6,749,559 B1 | 6/2004 | Kraas et al. |
| 6,749,560 B1 | 6/2004 | Konstorum et al. |
| 6,749,561 B2 | 6/2004 | Kazakevich |
| 6,749,601 B2 | 6/2004 | Chin |
| 6,752,758 B2 | 6/2004 | Motoki et al. |
| 6,753,905 B1 | 6/2004 | Okada et al. |
| 6,758,806 B2 | 7/2004 | Kamrava et al. |
| 6,758,807 B2 | 7/2004 | Minami |
| 6,758,842 B2 | 7/2004 | Irion et al. |
| 6,778,208 B2 | 8/2004 | Takeshige et al. |
| 6,780,151 B2 | 8/2004 | Grabover et al. |
| 6,785,410 B2 | 8/2004 | Vining et al. |
| 6,785,414 B1 | 8/2004 | McStravick et al. |
| 6,785,593 B2 | 8/2004 | Wang et al. |
| 6,793,622 B2 | 9/2004 | Konomrua et al. |
| 6,796,938 B2 | 9/2004 | Sendai |
| 6,796,939 B1 | 9/2004 | Hirata et al. |
| 6,798,533 B2 | 9/2004 | Tipirneni |
| 6,800,056 B2 | 10/2004 | Tartaglia et al. |
| 6,800,057 B2 | 10/2004 | Tsujita et al. |
| 6,808,491 B2 | 10/2004 | Kortenbach et al. |
| 6,811,532 B2 | 11/2004 | Ogura et al. |
| 6,824,539 B2 | 11/2004 | Novak |
| 6,824,548 B2 | 11/2004 | Smith et al. |
| 6,829,003 B2 | 12/2004 | Takami |
| 6,830,545 B2 | 12/2004 | Bendall |
| 6,832,990 B2 | 12/2004 | Kortenbach et al. |
| 6,840,932 B2 | 1/2005 | Lang et al. |
| 6,842,196 B1 | 1/2005 | Swift et al. |
| 6,846,285 B2 | 1/2005 | Hasegawa et al. |
| 6,846,286 B2 | 1/2005 | Suzuki et al. |
| 6,847,933 B1 | 1/2005 | Hastings |
| 6,849,043 B2 | 2/2005 | Kondo |
| 6,850,794 B2 | 2/2005 | Shahidi |
| 6,855,109 B2 | 2/2005 | Obata et al. |
| 6,856,436 B2 | 2/2005 | Brukilacchio et al. |
| 6,858,004 B1 | 2/2005 | Ozawa et al. |
| 6,858,005 B2 | 2/2005 | Ohline et al. |
| 6,858,014 B2 | 2/2005 | Damarati |
| 6,860,849 B2 | 3/2005 | Matsushita et al. |
| 6,863,650 B1 | 3/2005 | Irion |
| 6,863,661 B2 | 3/2005 | Carrillo et al. |
| 6,868,195 B2 | 3/2005 | Fujita |
| 6,871,086 B2 | 3/2005 | Nevo et al. |
| 6,871,993 B2 | 3/2005 | Hecht |
| 6,873,352 B2 | 3/2005 | Mochida et al. |
| 6,876,380 B2 | 4/2005 | Abe et al. |
| 6,879,339 B2 | 4/2005 | Ozawa |
| 6,881,188 B2 | 4/2005 | Furuya et al. |
| 6,882,785 B2 | 4/2005 | Eichelberger et al. |
| 6,887,195 B1 | 5/2005 | Pilvisto |
| 6,889,672 B2 | 5/2005 | Chin et al. |
| 6,890,294 B2 | 5/2005 | Niwa et al. |
| 6,892,090 B2 | 5/2005 | Verard et al. |
| 6,892,112 B2 | 5/2005 | Wang et al. |
| 6,895,268 B1 | 5/2005 | Rahn et al. |
| 6,898,086 B2 | 5/2005 | Takami et al. |
| 6,899,673 B2 | 5/2005 | Ogura et al. |
| 6,899,674 B2 | 5/2005 | Viebach et al. |
| 6,899,705 B2 | 5/2005 | Niemeyer |
| 6,900,829 B1 | 5/2005 | Ozawa et al. |
| 6,902,527 B1 | 6/2005 | Doguchi et al. |
| 6,902,529 B2 | 6/2005 | Onishi et al. |
| 6,903,761 B1 | 6/2005 | Abe et al. |
| 6,903,883 B2 | 6/2005 | Amanai |
| 6,905,057 B2 | 6/2005 | Swayze et al. |
| 6,905,462 B1 | 6/2005 | Homma |
| 6,908,307 B2 | 6/2005 | Keller et al. |
| 6,908,427 B2 | 6/2005 | Fleener et al. |
| 6,908,429 B2 | 6/2005 | Heimberger et al. |
| 6,911,916 B1 | 6/2005 | Wang et al. |
| 6,916,286 B2 | 7/2005 | Kazakevich |
| 6,923,818 B2 | 8/2005 | Muramatsu et al. |
| 6,928,490 B1 | 8/2005 | Bucholz et al. |
| 6,930,706 B2 | 8/2005 | Kobayashi et al. |
| 6,932,761 B2 | 8/2005 | Maeda et al. |
| 6,934,093 B2 | 8/2005 | Kislev et al. |
| 6,934,575 B2 | 8/2005 | Ferre et al. |
| 6,943,663 B2 | 9/2005 | Wang et al. |
| 6,943,821 B2 | 9/2005 | Abe et al. |
| 6,943,822 B2 | 9/2005 | Iida et al. |
| 6,943,946 B2 | 9/2005 | Fiete |
| 6,943,959 B2 | 9/2005 | Homma |
| 6,943,966 B2 | 9/2005 | Konno |
| 6,944,031 B2 | 9/2005 | Takami et al. |
| 6,949,068 B2 | 9/2005 | Taniguchi et al. |
| 6,950,248 B2 | 9/2005 | Rudischhauser et al. |
| 6,950,691 B2 | 9/2005 | Uchikubo |
| 6,954,311 B2 | 10/2005 | Amanai |
| 6,955,671 B2 | 10/2005 | Uchikubo |
| 6,956,703 B2 | 10/2005 | Saito |
| 6,960,161 B2 | 11/2005 | Amling et al. |
| 6,961,187 B2 | 11/2005 | Amanai |
| 6,962,564 B2 | 11/2005 | Hickle |
| 6,963,175 B2 | 11/2005 | Archenhold et al. |
| 6,964,662 B2 | 11/2005 | Kidooka et al. |
| 6,967,673 B2 | 11/2005 | Ozawa et al. |
| 6,974,466 B2 | 12/2005 | Ahmed et al. |
| 6,975,968 B2 | 12/2005 | Nakamitsu et al. |
| 6,976,954 B2 | 12/2005 | Takahashi |
| 6,977,053 B2 | 12/2005 | Mukasa et al. |
| 6,977,670 B2 | 12/2005 | Takahashi et al. |
| 6,980,227 B2 | 12/2005 | Iida et al. |
| 6,980,921 B2 | 12/2005 | Anderson et al. |
| 6,981,945 B1 | 1/2006 | Sarvazyan et al. |
| 6,982,740 B2 | 1/2006 | Adair et al. |
| 6,984,206 B2 | 1/2006 | Kumei et al. |
| 6,985,183 B2 | 1/2006 | Jan et al. |
| 6,986,686 B2 | 1/2006 | Shibata et al. |
| 6,994,668 B2 | 2/2006 | Miyano |
| 6,994,704 B2 | 2/2006 | Qin et al. |
| 7,001,330 B2 | 2/2006 | Kobayashi |
| 7,008,376 B2 | 3/2006 | Ikeda et al. |
| 7,024,573 B2 | 4/2006 | Patel et al. |
| 7,090,637 B2 | 8/2006 | Danitz et al. |
| 7,169,167 B2 | 1/2007 | Chu |
| 7,591,783 B2 | 9/2009 | Boulais et al. |
| 7,637,905 B2 | 12/2009 | Saadat et al. |
| 2001/0025135 A1 | 9/2001 | Naito et al. |
| 2001/0031912 A1 | 10/2001 | Adler |
| 2001/0039370 A1 | 11/2001 | Takahashi et al. |
| 2001/0049491 A1 | 12/2001 | Shimada |
| 2002/0017515 A1 | 2/2002 | Obata et al. |
| 2002/0028984 A1 | 3/2002 | Hayakawa et al. |
| 2002/0055669 A1 | 5/2002 | Konno |
| 2002/0080248 A1 | 6/2002 | Adair et al. |
| 2002/0087048 A1 | 7/2002 | Brock et al. |
| 2002/0087166 A1 | 7/2002 | Brock et al. |
| 2002/0095175 A1 | 7/2002 | Brock et al. |
| 2002/0128633 A1 | 9/2002 | Brock et al. |
| 2002/0147481 A1 | 10/2002 | Brugger et al. |
| 2002/0163575 A1 | 11/2002 | Ayame et al. |
| 2002/0165432 A1 | 11/2002 | Matsui |
| 2002/0193662 A1 | 12/2002 | Belson |
| 2002/0193664 A1 | 12/2002 | Ross et al. |
| 2003/0032860 A1 | 2/2003 | Avni et al. |
| 2003/0034863 A1 | 2/2003 | Kazakevich |
| 2003/0045778 A1 | 3/2003 | Ohline et al. |

(56) References Cited

U.S. PATENT DOCUMENTS

| | | |
|---|---|---|
| 2003/0065250 A1 | 4/2003 | Chiel et al. |
| 2003/0069897 A1 | 4/2003 | Roy et al. |
| 2003/0083550 A1 | 5/2003 | Miyagi |
| 2003/0125606 A1 | 7/2003 | Amling et al. |
| 2003/0149338 A1 | 8/2003 | Francois et al. |
| 2003/0163025 A1 | 8/2003 | Kaji |
| 2003/0181905 A1 | 9/2003 | Long |
| 2004/0015079 A1 | 1/2004 | Berger |
| 2004/0049097 A1 | 3/2004 | Miyake |
| 2004/0054258 A1 | 3/2004 | Maeda et al. |
| 2004/0073083 A1 | 4/2004 | Ikeda et al. |
| 2004/0073084 A1 | 4/2004 | Maeda et al. |
| 2004/0073085 A1 | 4/2004 | Ikeda et al. |
| 2004/0124157 A1 | 7/2004 | Briggs et al. |
| 2004/0143159 A1 | 7/2004 | Wendlandt |
| 2004/0147809 A1 | 7/2004 | Kazakevich |
| 2004/0167379 A1 | 8/2004 | Akiba |
| 2004/0170017 A1 | 9/2004 | Zhan et al. |
| 2004/0186349 A1 | 9/2004 | Ewers et al. |
| 2004/0190305 A1 | 9/2004 | Arik et al. |
| 2004/0193016 A1 | 9/2004 | Root et al. |
| 2004/0249247 A1 | 12/2004 | Iddan |
| 2004/0257608 A1 | 12/2004 | Tipimeni |
| 2005/0030754 A1 | 2/2005 | Licht |
| 2005/0075538 A1 | 4/2005 | Banik et al. |
| 2005/0137459 A1 | 6/2005 | Chin et al. |
| 2005/0180136 A9 | 8/2005 | Popovich |
| 2005/0192476 A1 | 9/2005 | Homan et al. |
| 2005/0197861 A1 | 9/2005 | Omori et al. |
| 2005/0200698 A1 | 9/2005 | Amling et al. |
| 2005/0203341 A1 | 9/2005 | Welker et al. |
| 2005/0203418 A1 | 9/2005 | Yamada et al. |
| 2005/0205958 A1 | 9/2005 | Taniguchi et al. |
| 2005/0207645 A1 | 9/2005 | Nishimura et al. |
| 2005/0209509 A1 | 9/2005 | Belson |
| 2005/0225872 A1 | 10/2005 | Uzawa et al. |
| 2005/0226508 A1 | 10/2005 | Gotohda |
| 2005/0228221 A1 | 10/2005 | Hirakawa |
| 2005/0228222 A1 | 10/2005 | Furumi |
| 2005/0228227 A1 | 10/2005 | Weber |
| 2005/0228697 A1 | 10/2005 | Funahashi |
| 2005/0231591 A1 | 10/2005 | Abe |
| 2005/0234507 A1 | 10/2005 | Geske et al. |
| 2005/0243169 A1 | 11/2005 | Ono et al. |
| 2005/0247081 A1 | 11/2005 | Sakata et al. |
| 2005/0250983 A1 | 11/2005 | Tremaglio et al. |
| 2005/0251112 A1 | 11/2005 | Danitz et al. |
| 2005/0251998 A1 | 11/2005 | Bar-Or et al. |
| 2005/0253044 A1 | 11/2005 | Kuriyama |
| 2005/0256370 A1 | 11/2005 | Fujita |
| 2005/0256373 A1 | 11/2005 | Bar-Or et al. |
| 2005/0256377 A1 | 11/2005 | Deppmeier et al. |
| 2005/0256424 A1 | 11/2005 | Zimmon |
| 2005/0264687 A1 | 12/2005 | Murayama |
| 2005/0267417 A1 | 12/2005 | Secrest et al. |
| 2005/0271340 A1 | 12/2005 | Weisburg et al. |
| 2005/0272978 A1 | 12/2005 | Brunnen et al. |
| 2005/0273085 A1 | 12/2005 | Hinmane et al. |
| 2005/0288545 A1 | 12/2005 | Matsumoto et al. |
| 2005/0288553 A1 | 12/2005 | Sugimoto |
| 2006/0015008 A1 | 1/2006 | Kennedy |

FOREIGN PATENT DOCUMENTS

| | | |
|---|---|---|
| EP | 0 437 229 | 7/1991 |
| EP | 0 689 851 | 1/1996 |
| EP | 0 728 487 | 8/1996 |
| EP | 1 300 883 | 4/2003 |
| EP | 1 433 412 | 6/2004 |
| JP | 58-78635 | 5/1983 |
| JP | 4-12725 | 1/1992 |
| JP | 4-28335 | 1/1992 |
| JP | 05-31071 | 2/1993 |
| JP | 05-091972 | 4/1993 |
| JP | 06-105800 | 4/1994 |
| JP | 3372273 | 4/1994 |
| JP | 06-254048 | 9/1994 |
| JP | 3219521 | 9/1994 |
| JP | 07-8441 | 1/1995 |
| JP | 7-12102 | 2/1995 |
| JP | 3482238 | 12/1995 |
| JP | 10-113330 | 5/1998 |
| JP | 10-286221 | 10/1998 |
| JP | 11-216113 | 8/1999 |
| JP | 2001 128933 | 5/2001 |
| JP | 2002 078675 | 3/2002 |
| JP | 2002-102152 | 4/2002 |
| JP | 2002-177197 | 6/2002 |
| JP | 2002-185873 | 6/2002 |
| JP | 2002-253481 | 9/2002 |
| JP | 2003-75113 | 3/2003 |
| JP | 2002 007134 | 7/2003 |
| JP | 2003-348454 | 12/2003 |
| WO | WO 93/13704 | 7/1993 |
| WO | WO 03/097156 | 11/2003 |
| WO | WO 2004/016310 | 2/2004 |
| WO | WO 2005/023082 | 3/2005 |

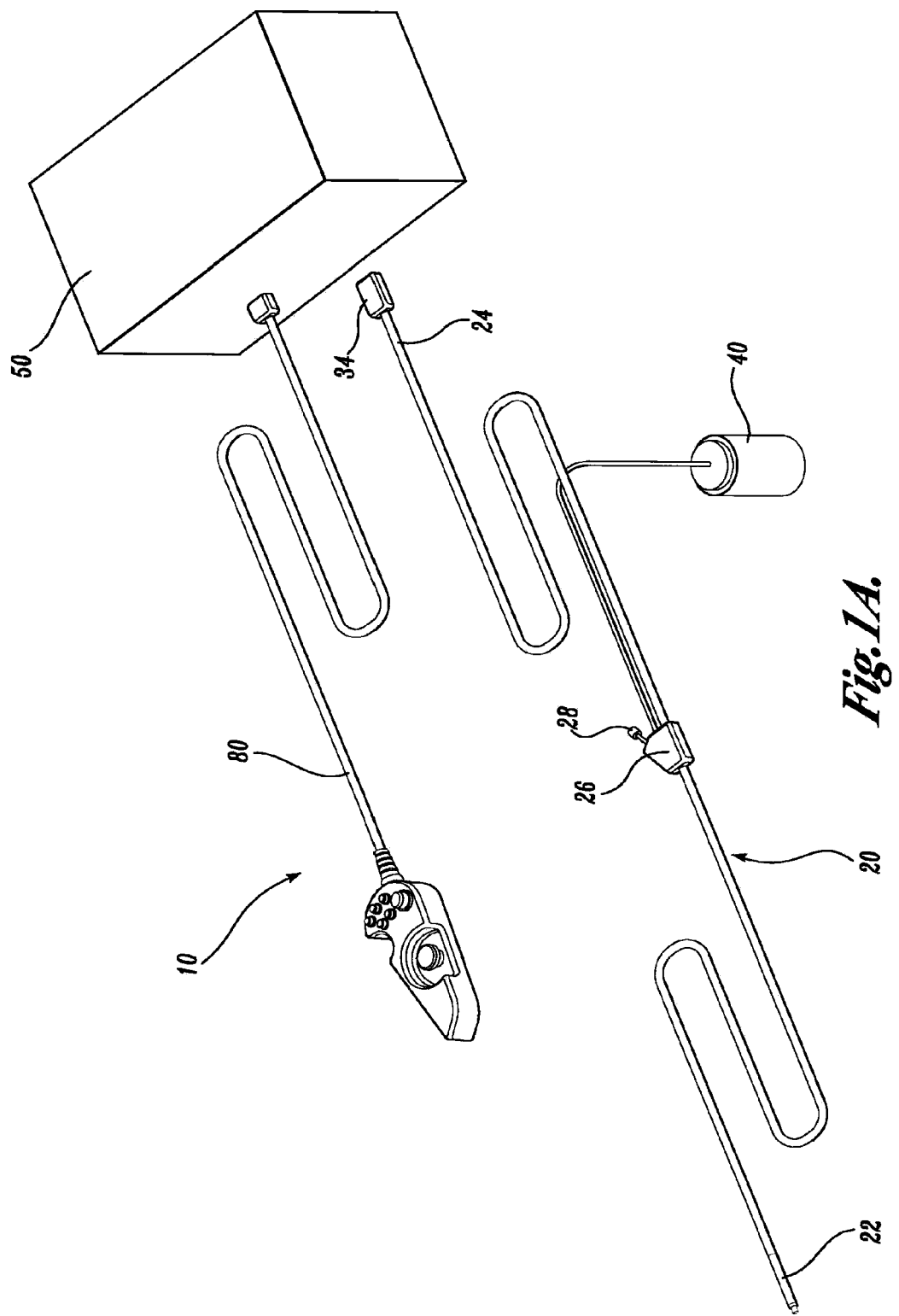

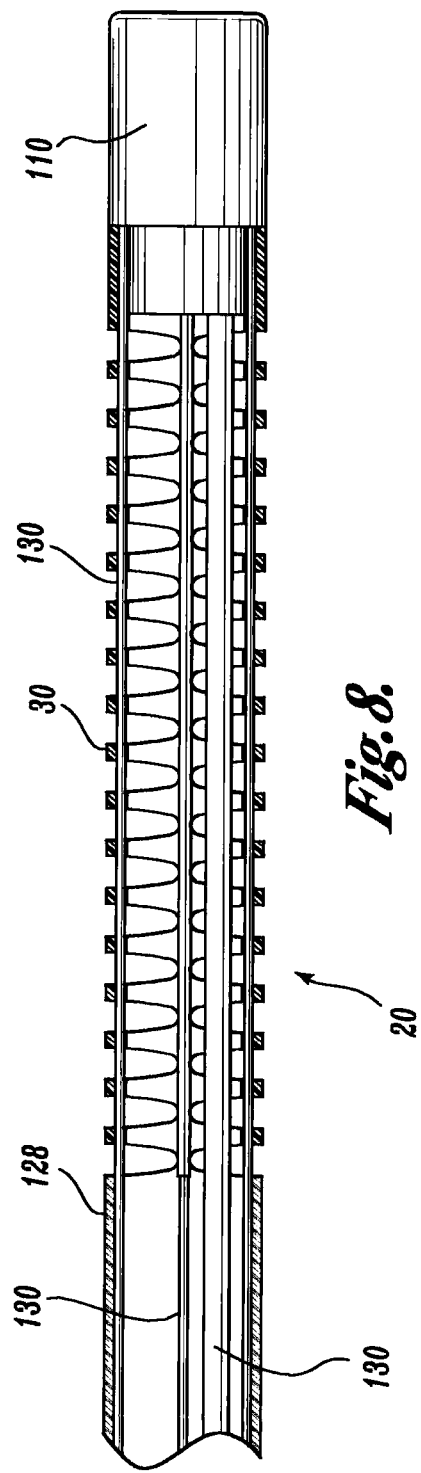
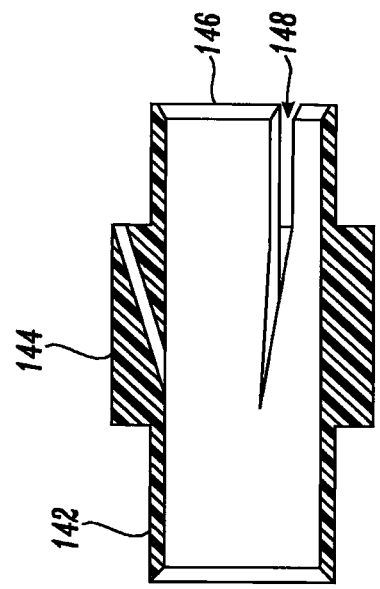
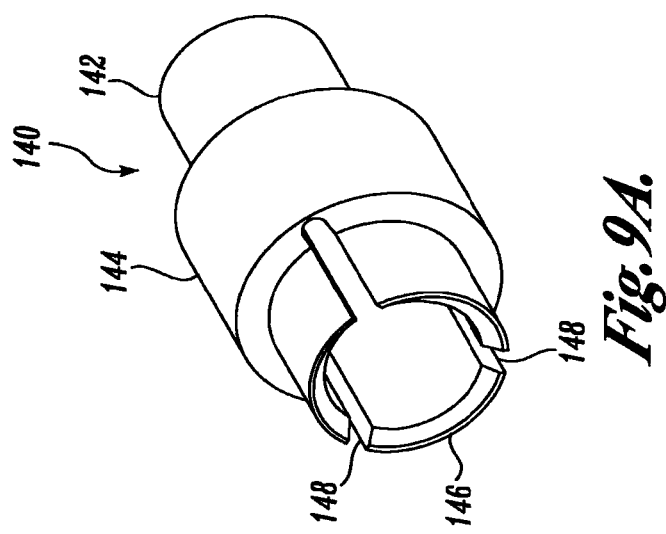

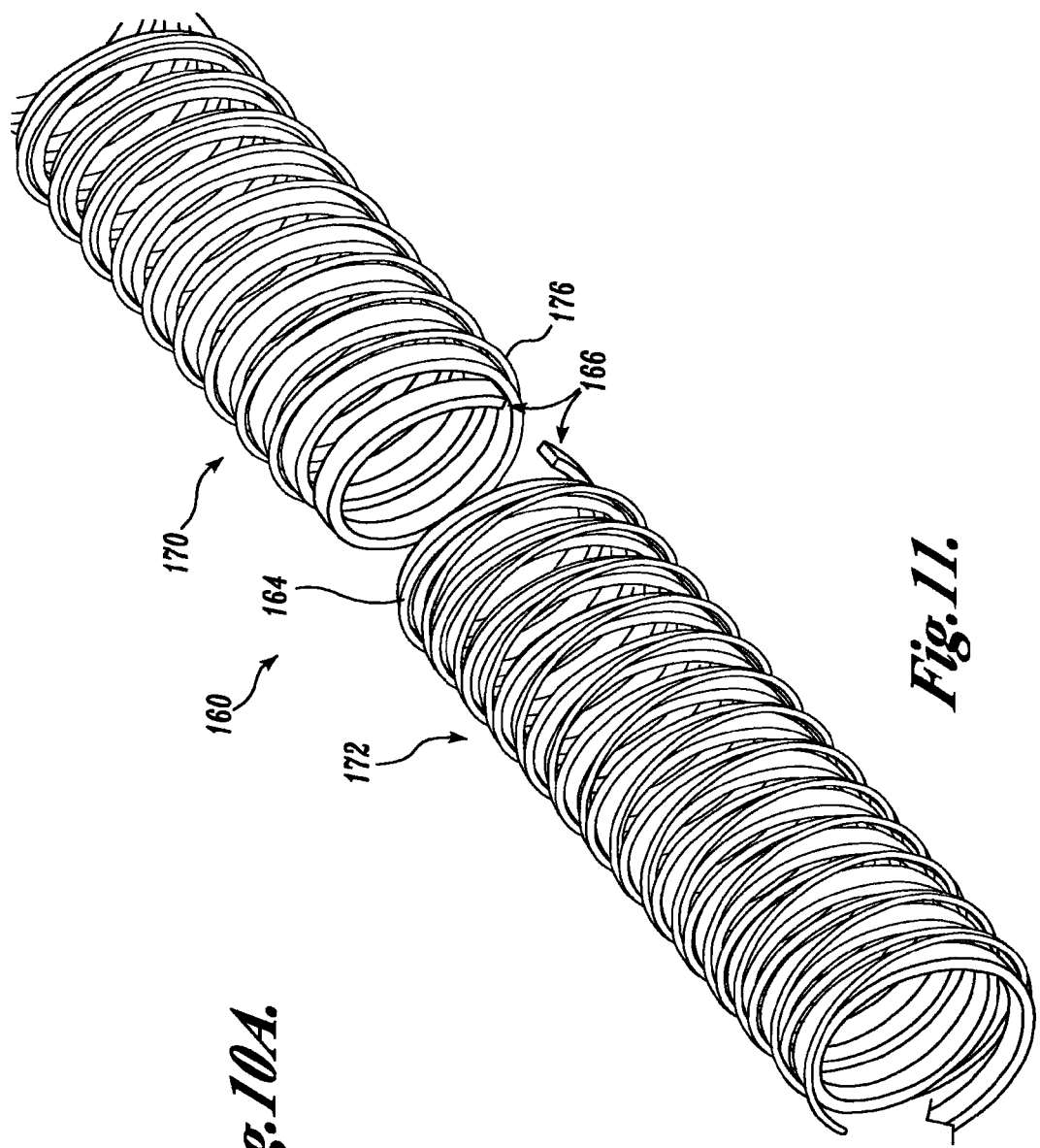
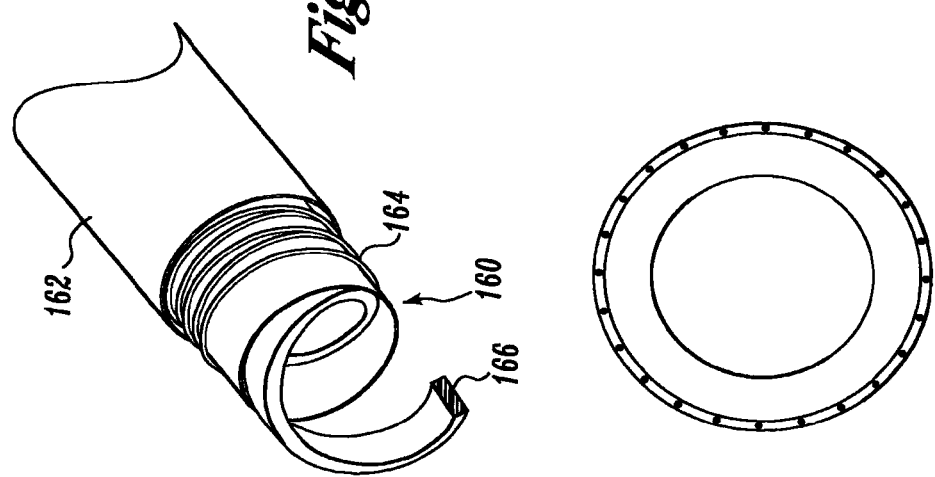

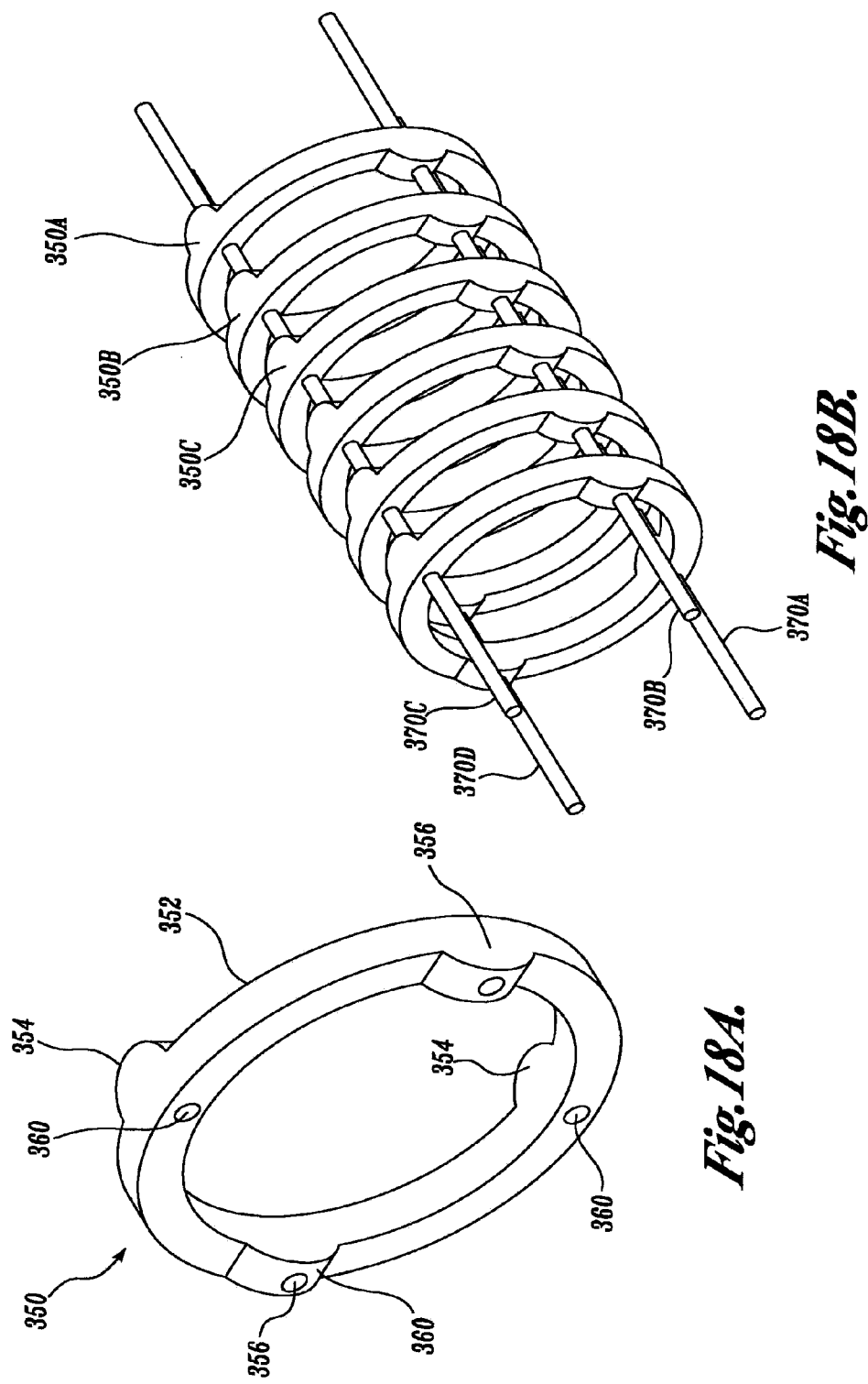

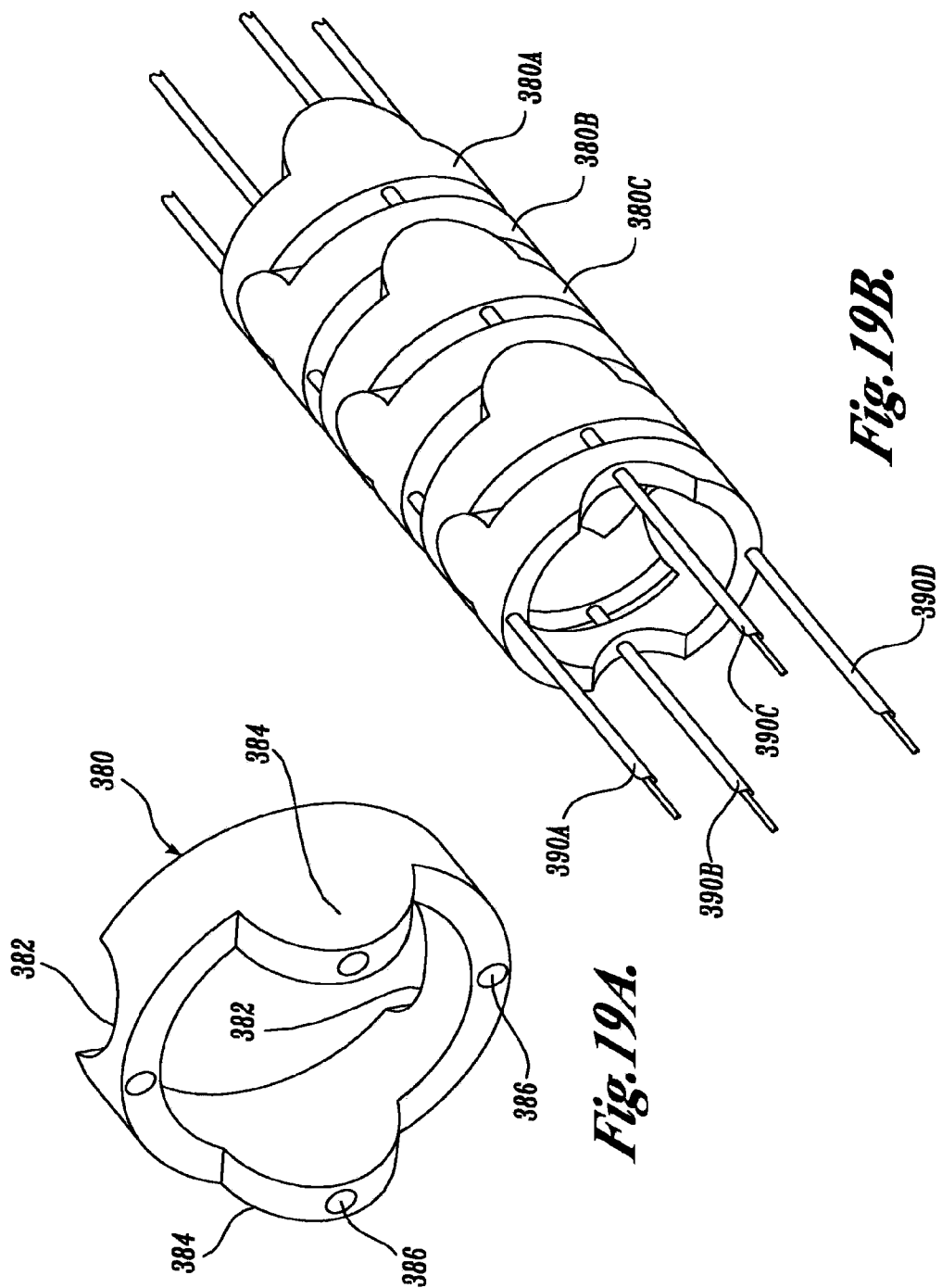

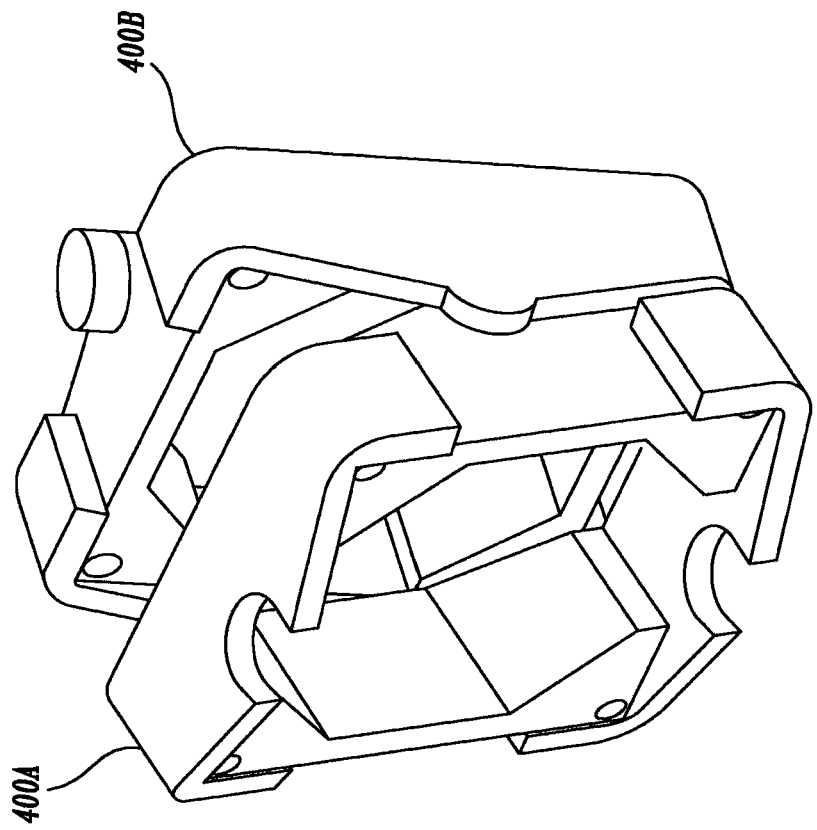
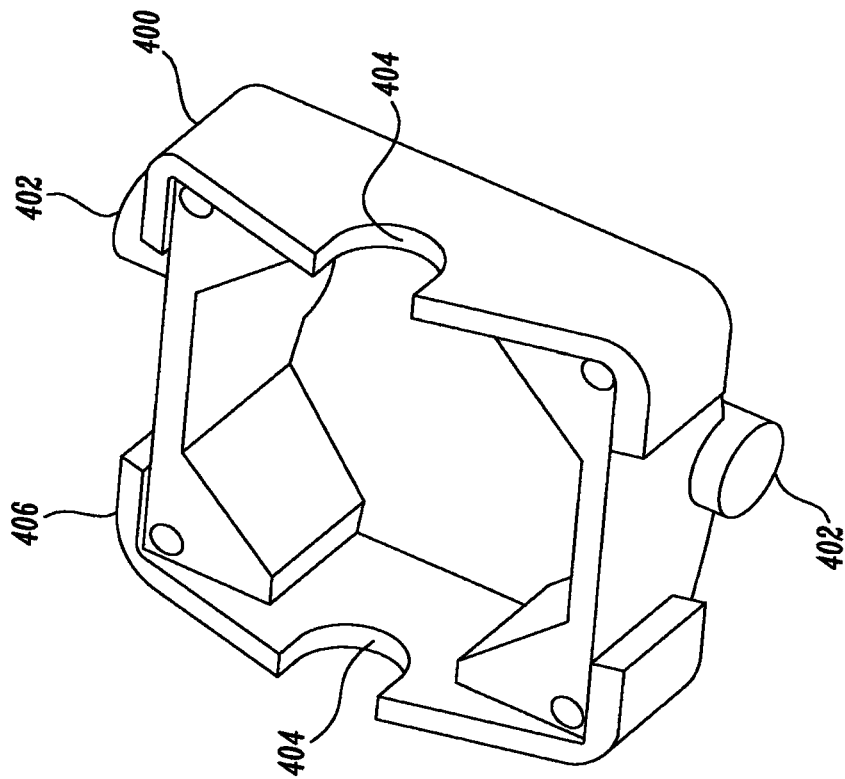
*Fig.21B.*
*Fig.21A.*

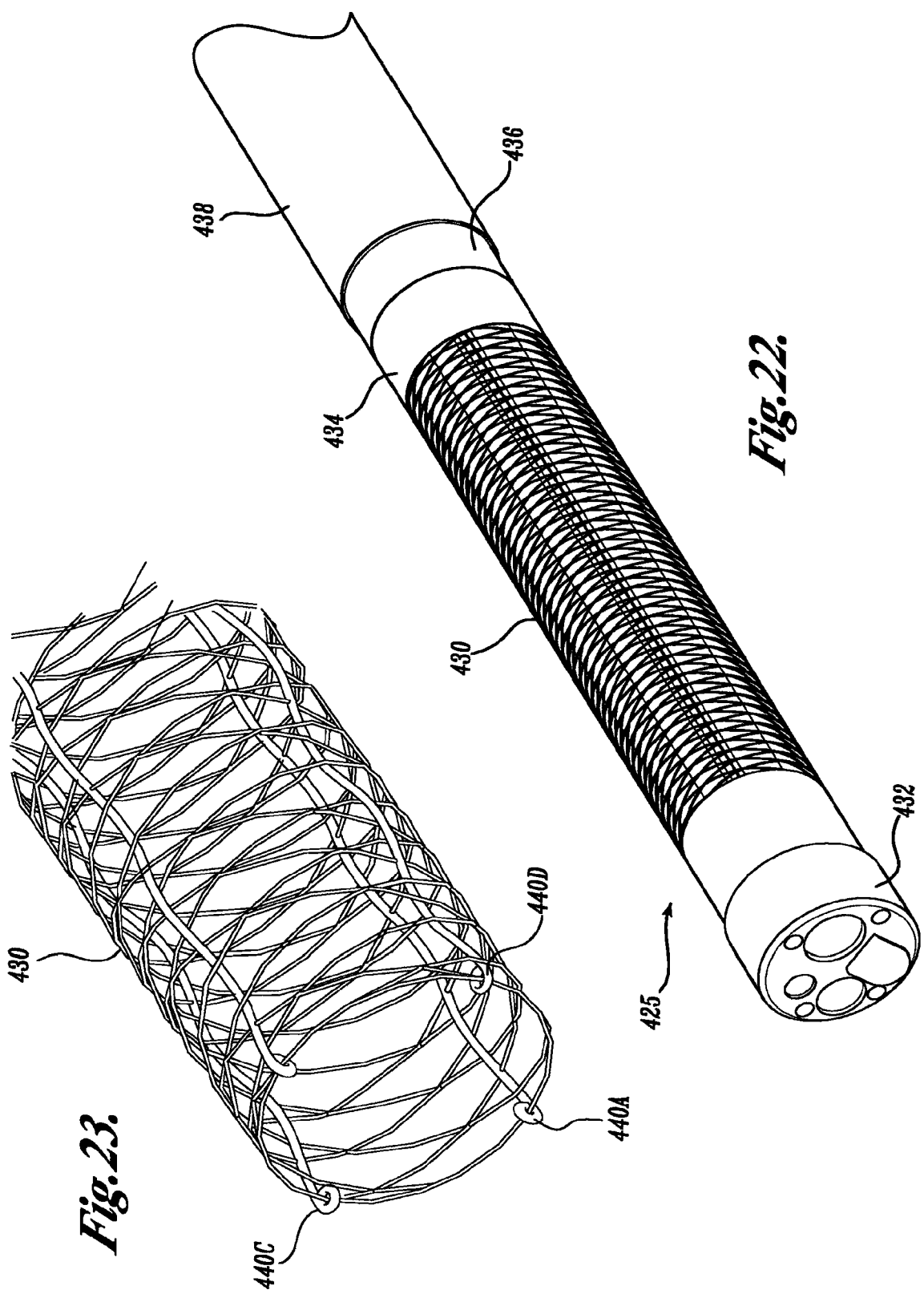

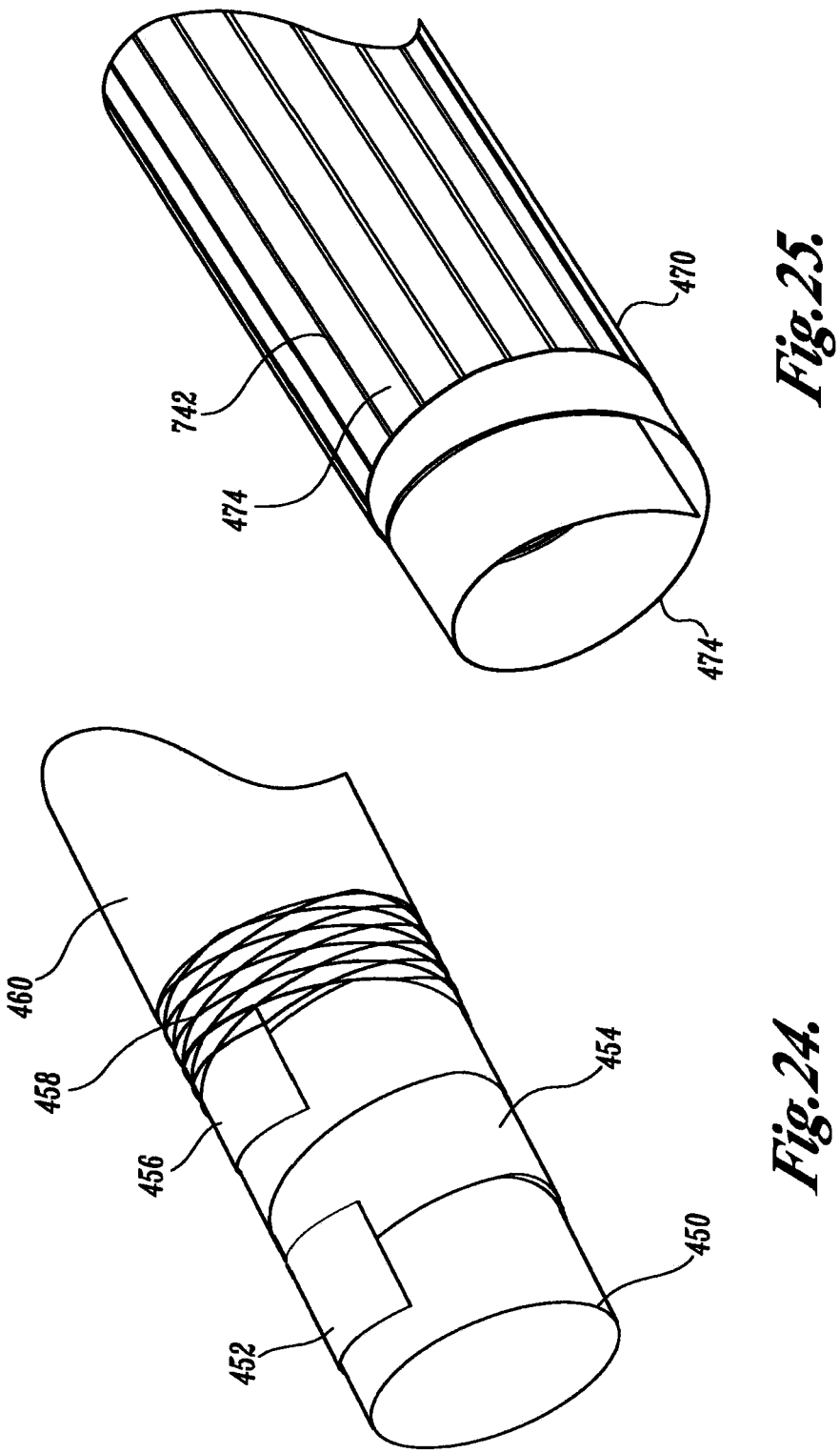

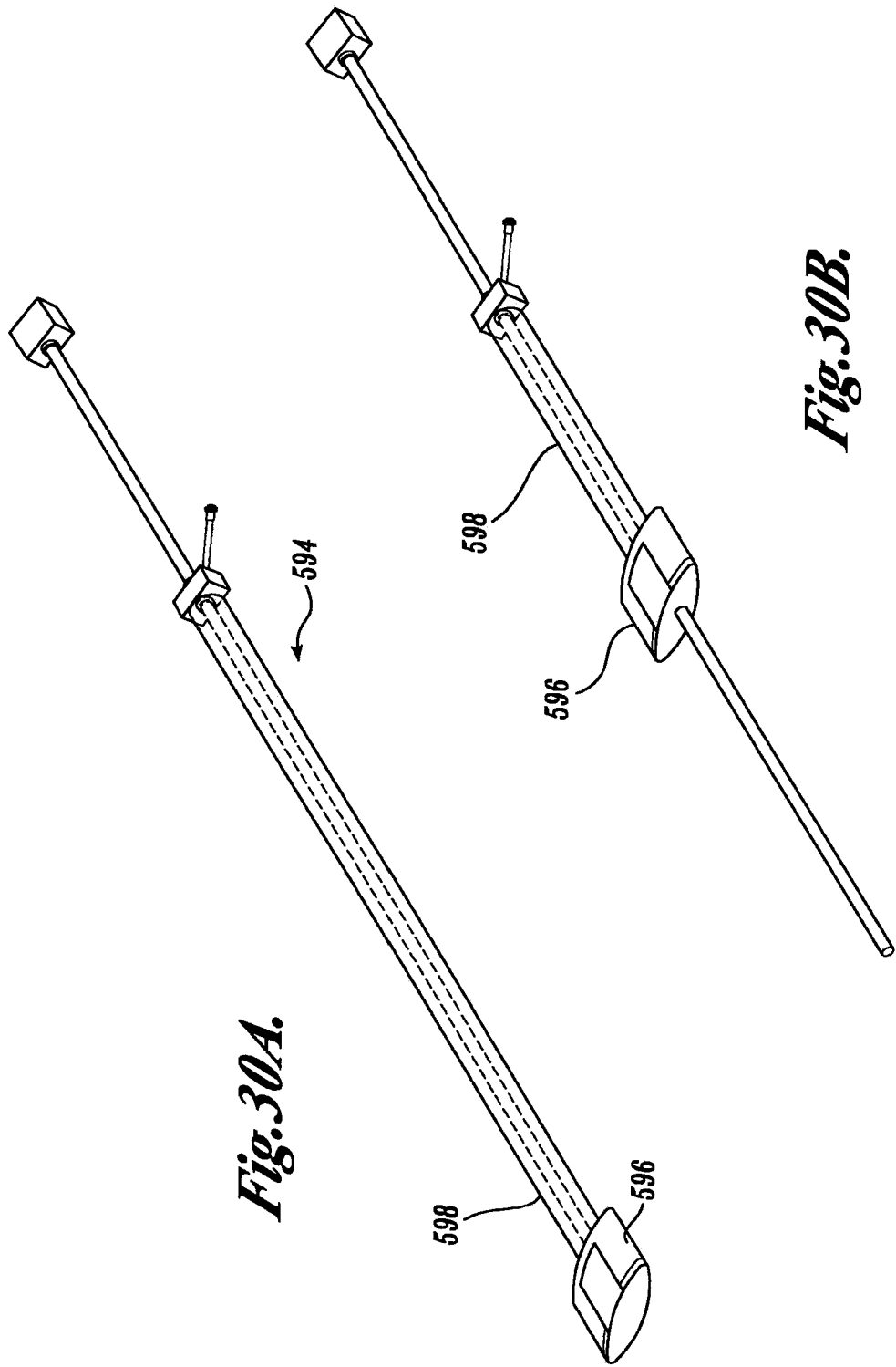

ARTICULATION JOINT

CROSS-REFERENCE TO RELATED APPLICATIONS

This application is a continuation of U.S. patent application Ser. No. 12/111,082, filed on Apr. 28, 2008 now abandoned, which is a continuation of U.S. patent application Ser. No. 10/406,149, filed on Apr. 1, 2003 now abandoned, all of which are incorporated herein by reference in their entirety.

FIELD OF THE INVENTION

The present invention relates to medical devices in general and therapeutic and diagnostic endoscopes in particular.

BACKGROUND OF THE INVENTION

As an aid to the early detection of disease, it has become well established that there are major public health benefits from regular endoscopic examinations of internal structures such as the esophagus, lungs, colon, uterus, and other organ systems. A conventional imaging endoscope used for such procedures comprises a flexible tube with a fiber optic light guide that directs illuminating light from an external light source through a lens at the distal end of the endoscope which focuses the illumination on the tissue to be examined. An objective lens and fiber optic imaging light guide communicating with a camera at the proximal end of the scope, or an imaging camera chip at the distal tip, transmit an image to the examiner. In addition, most endoscopes include one or more working channels through which medical devices such as biopsy forceps, snares, fulguration probes, and other tools may be passed.

Navigation of the endoscope through complex and tortuous paths is critical to success of the examination with minimum pain, side effects, risk or sedation to the patient. To this end, modern endoscopes include means for deflecting the distal tip of the scope to follow the pathway of the structure under examination, with minimum deflection or friction force upon the surrounding tissue. Control cables similar to puppet strings are carried within the endoscope body and connect a flexible portion of the distal end to a set of control knobs at the proximal endoscope handle. By manipulating the control knobs, the examiner is usually able to steer the endoscope during insertion and direct it to the region of interest, in spite of the limitations of such traditional control systems, which are clumsy, non-intuitive, and friction-limited. Common operator complaints about traditional endoscopes include their limited flexibility, limited column strength, and limited operator control of stiffness along the scope length.

Conventional endoscopes are expensive medical devices costing in the range of $25,000 for an endoscope, and much more for the associated operator console. Because of the expense, these endoscopes are built to withstand repeated disinfections and use upon many patients. Conventional endoscopes are generally built of sturdy materials, which decreases the flexibility of the scope and thus can decrease patient comfort. Furthermore, conventional endoscopes are complex and fragile instruments which can frequently need expensive repair as a result of damage during use or during a disinfection procedure. To overcome these and other problems, there is a need for a low cost imaging endoscope that can be used for a single procedure and thrown away. The scope should have better navigation and tracking, a superior interface with the operator, improved access by reduced frictional forces upon the lumenal tissue, increased patient comfort, and greater clinical productivity and patient throughput than those that are currently available.

SUMMARY OF THE INVENTION

To address these and other problems in the prior art, the present invention is an endoscopic video imaging system. The system includes a motion control cabinet that includes a number of actuators that control the orientation of an endoscope and an imaging system to produce images of tissue collected by an image sensor at the distal end of the endoscope. A single use endoscope is connectable with the control cabinet and used to examine a patient. After the examination procedure, the endoscope is disconnected and disposed of.

The endoscope of the present invention includes a flexible elongate tube or shaft and an illumination source that directs light onto a tissue sample. An image sensor and objective lens at or adjacent the distal end of the endoscope captures reflected light to produce an image of the illuminated tissue. Images produced by the sensor are transmitted to a display device to be viewed by an examiner. In one embodiment, the illumination source comprises one or more light emitting diodes (LEDs) and the image sensor comprises a CMOS solid state image sensor.

The endoscope of the present invention also includes a steering mechanism such as a number of tensile control cables, which allow the distal end of the endoscope to be deflected in a desired direction. In one embodiment of the invention, a proximal end of the tensile control cables communicates with actuators within the control cabinet. A freestanding joystick controller generates electrical control signals which the control cabinet uses to compute signals to drive the actuators that orient the distal end of the endoscope in the direction desired by the examiner. In another embodiment of the invention, the distal end of the endoscope is automatically steered, or provided to the examiner, based on analysis of images from the image sensor.

In one embodiment of the invention, the endoscope includes a polymeric articulation joint adjacent its distal end that aids in bending the distal end of the scope in a desired direction. The articulation joint is constructed as a number of live hinges integrated into a unified structure of the required overall properties and dimensions. Tension of the control cables causes the live hinges of the articulation joint to deflect, thereby bending the distal tip of the endoscope. In one embodiment of the invention, the articulation joint exerts a restoring force such that upon release of a tensioning force, the distal end of the scope will straighten.

In an alternative embodiment, the articulation joint comprises a number of stacked discs that rotate with respect to one another. Control cables pass through the discs and pull adjacent discs together to turn the distal end of the endoscope.

In another embodiment of the invention, the endoscope has a variation in stiffness along its length that allows the distal end to be relatively flexible while the more proximal regions of the scope have increased column strength and torque fidelity so that a physician can twist and advance the endoscope with greater ease and accuracy and with fewer false advances ("loops"). Variation in stiffness along the length can be provided by varying the durometer of materials that comprise a shaft of the endoscope. Operator-controlled, variable stiffness can be provided by control cables that can be tightened or loosened to adjust the stiffness of the shaft. In yet another embodiment, the spacing between the live hinges of the articulation joint is selected to provide a variation in stiffness along the length of the articulation joint.

In yet another embodiment of the invention, the endoscope is covered with a retractable sleeve that uncovers the distal end of the scope during use and extends over the distal end after the scope is removed from a patient.

In another embodiment of the invention, the scope is coated with a hydrophilic coating to reduce its coefficient of friction.

In another embodiment of the invention, the scope is retractable in a longitudinal direction. The distal end of the scope is extendable using a spring, pull wires, bellows or the like to allow a physician to move the distal tip without having to alter the position of the shaft of the endoscope.

In yet another embodiment of the invention, the endoscope includes a heat dissipating mechanism for removing heat produced by the illumination source and image sensor.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 1A and 1B illustrate two possible embodiments of an endoscopic video imaging system in accordance with the present invention;

FIG. 8 illustrates an imaging endoscope having control cables routed through lumens in the walls of an endoscope shaft;

FIGS. 9A and 9B illustrate a transition guide that routes control cables from a central lumen of an endoscope shaft to lumens in an articulation joint;

FIGS. 10A and 10B illustrate the construction of a shaft portion of an endoscope in accordance with one embodiment of the present invention;

FIG. 11 illustrates one mechanism for providing a shaft having a varying stiffness along its length;

FIGS. 18A-18B illustrate an articulation joint formed of a number of stacked discs in accordance with another embodiment of the present invention;

FIGS. 19A-19B illustrate a disc used to form an articulation joint in accordance with another embodiment of the present invention;

FIGS. 21A-21B illustrate a non-circular segment used to form an articulation joint in accordance with another embodiment of the present invention;

FIG. 22 illustrates an endoscope having a braided member as an articulation joint in accordance with another embodiment of the present invention;

FIG. 23 illustrates one possible technique for securing the ends of a control wire to a braided articulation joint;

FIG. 24 illustrates a shaft having one or more memory reducing wraps in accordance with another embodiment of the present invention;

FIG. 25 illustrates a shaft including longitudinal stripes of a high durometer material in accordance with another embodiment of the present invention;

FIGS. 30A and 30B illustrate a retractable sleeve used with another embodiment of the present invention;

DETAILED DESCRIPTION OF THE PREFERRED EMBODIMENT

Figure 1B:
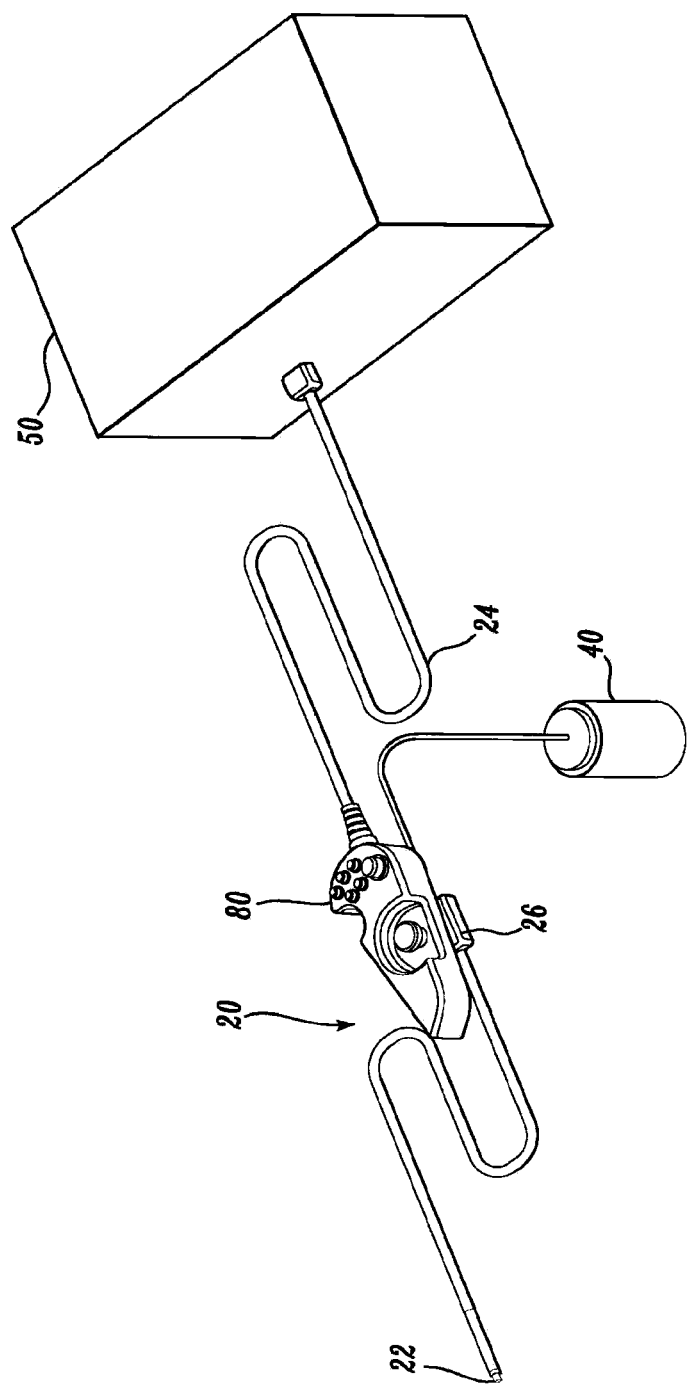

As indicated above, the present invention is an endoscopic video imaging system that allows a physician to view internal body cavities of a patient as well as to insert surgical instruments into the patient's body. An imaging endoscope used with the present invention is sufficiently inexpensive to manufacture such that the endoscope can be considered a disposable item.

As shown in FIG. 1A, an endoscopic video imaging system 10 according to one embodiment of the present invention includes an imaging endoscope 20, a motion control cabinet 50 and a handheld controller 80. The imaging endoscope 20 has a distal tip 22 that is advanced into a patient's body cavity and a proximal end 24 that is connected to the motion control cabinet 50. As will be explained in further detail below, the motion control cabinet 50 includes a number of actuators that control a steering mechanism within the endoscope in order to change the orientation of the distal tip 22. A physician or their assistant uses the handheld controller 80 to input control signals that move the distal tip 22 of the imaging endoscope 20. In addition, the motion control cabinet 50 may include connections to sources of air/gas and a flushing liquid such as water for clearing the imaging endoscope. The motion control cabinet 50 also includes imaging electronics to create and/or transfer images received from an image sensor to a video display for viewing by a physician or technician.

In the embodiment shown, the imaging endoscope 20 also includes a breakout box 26 that is positioned approximately midway along the length of the endoscope. The breakout box 26 provides an attachment point for a vacuum bottle 40 that collects liquids from a lumen within the imaging endoscope. The vacuum bottle 40 is controlled by a vacuum valve 28 that is positioned on the breakout box 26. Alternatively, the valve can be positioned within the motion control cabinet 50 and controlled from the handheld controller 80.

If desired, the handheld controller 80 can be secured to the breakout box 26 such that the two units can be moved as one if desired. Upon completion of a patient examination procedure, the imaging endoscope 20 is disconnected from the motion control cabinet 50 and disposed of. A new imaging endoscope 20 is then connected to the motion control cabinet 50 for the next examination procedure to be performed.

The embodiment shown in FIG. 1A is a "parallel" configuration whereby the endoscope 20 and handheld controller 80 are separately plugged into different connectors of the motion control cabinet 50. This parallel configuration allows one operator to handle the endoscope while another operator can handle the handheld controller 80. Alternatively, the handheld controller 80 may be secured to the endoscope 20 such that a single operator can control both. FIG. 1B illustrates a "serial" configuration of the invention. Here, the imaging endoscope 20 is connected to the motion control cabinet 50 through the handheld controller 80.

Figure 2:
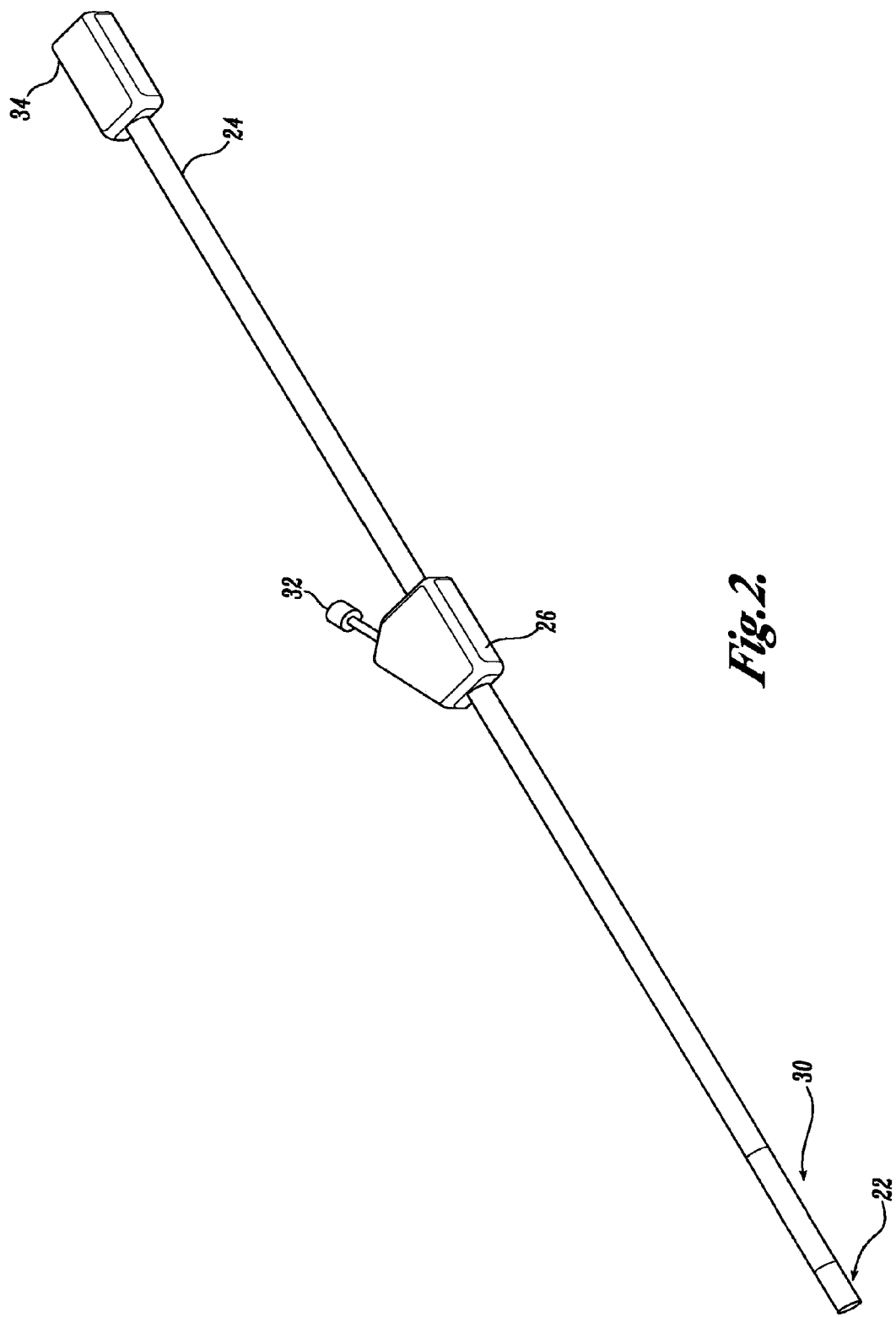
FIG. 2 illustrates further detail of an endoscope used in the imaging system shown in FIG. 1A.

FIG. 2 shows further detail of one embodiment of the imaging endoscope 20. At the proximal end of the endoscope is a low torque shaft 24 and a connector 34 that connects the endoscope 20 to the motion control cabinet 50. Distal to the breakout box 26 is a higher torque shaft. At the distal end of the endoscope 20 is the distal tip 22 that includes a light illumination port, an image sensor, an entrance to a working lumen and a flushing lumen (not shown). Proximal to the distal tip 22 is an articulation joint 30 that provides sufficient flexibility to the distal section of the shaft such that the distal tip 22 can be directed over an angle of 180 degrees by the steering mechanism.

As discussed above, the endoscope 20, in accordance with one embodiment of the invention, has a higher torque shaft at the distal section of the endoscope and a lower torque shaft at its proximal end. The breakout box 26 positioned along the length of the endoscope shaft can be used as a handle or gripper to impart rotation of the distal end of the endoscope during a medical examination procedure. The higher torque portion of the shaft transfers rotational motion that is imparted at a location proximal to the distal tip in order to guide the distal tip of the imaging catheter. The low torque shaft portion of the imaging catheter does not transfer torque as well and can twist when rotational motion is applied.

In use, the physician can insert a medical device such as a biopsy forceps, snare, etc., into a connector 32 found on the breakout box 26 that leads to a working channel lumen in the endoscope. In alternate embodiments, the entrance to the working channel lumen may be positioned further towards the proximal end of the endoscope.

Figure 3A:
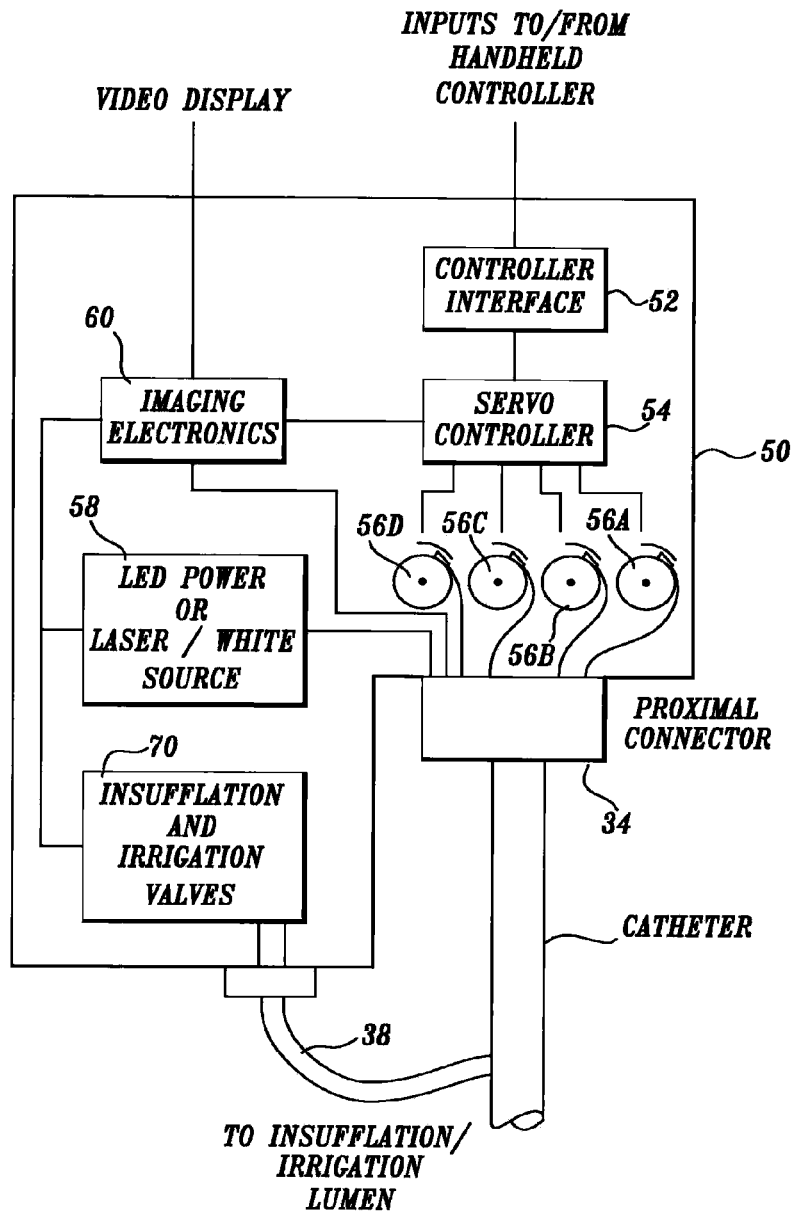
FIG. 3A is a block diagram of a motion control cabinet that interfaces with an imaging endoscope in accordance with one embodiment of the present invention.

FIG. 3A is a block diagram of the major components included within one embodiment of the motion control cabinet 50. The motion control cabinet is preferably positioned on a cart that is wheeled near a patient prior to an examination procedure. The motion control cabinet is connected to a source of electrical power, either A.C. mains or a battery, as well as to a source of insufflation gas and irrigation liquid. Inside the motion control cabinet 50 is a controller interface 52 that is connected to the handheld controller 80 and receives control signals therefrom. To change the orientation of the distal tip of the imaging endoscope, the control signals are received from a directional switch in the handheld controller 80. The control signals are supplied to a servo motor controller 54 that in turn controls a number of actuators, such as servo motors 56a, 56b, 56c, 56d. Each of the servo motors 56a-56d is connected to one or more control cables within the imaging endoscope. Motion of the servo motors 56a-56d pulls or releases the control cables in order to change the orientation of the distal tip 22 of the imaging endoscope 20. Although the embodiment shown in FIG. 3A shows four servo motors and control cables, it will be appreciated that fewer or more servo motors and corresponding control cables could be used to move the distal tip. For example, some imaging endoscopes may use three control cables and three associated servo motors.

Also included in the motion control cabinet 50 is a power source 58 that provides electrical power to a light source such as a number of light emitting diodes (LEDs) at the distal end 22 of the imaging endoscope. Alternatively, if the imaging catheter utilizes an external light source, then the motion control cabinet can include a high intensity light source such as a laser or Xenon white light source that supplies light to a fiber optic illumination guide within the imaging endoscope 20 in order to illuminate an internal body organ. The power source 58 may be controlled by control signals received from the handheld controller 80 when the user desires to activate the light source.

An imaging electronics board 60 captures images received from an image sensor (not shown) at the distal end of the imaging endoscope. The imaging electronics board 60 can enhance the images received or can provide video effects such as zoom, color changes, highlighting, etc., prior to display of the images on a video display (not shown). Images of the tissue may also be analyzed by the imaging electronics board 60 to produce control signals that are supplied to the servo motor controller 54 in order to automatically steer the distal tip of the endoscope as will be discussed in further detail below. Images produced by the imaging electronics board 60 may also be printed on a digital printer, saved to a computer readable media such as a floppy disk, CD, DVD, etc., or a video tape for later retrieval and analysis by a physician.

Finally, the motion control cabinet 50 includes valves 70 that control the delivery of insufflation air/gas to insufflate a patient's body cavity and an irrigation liquid to flush out a body cavity and/or clean the imaging light source and image sensor at the distal end of the endoscope. The insufflation air/gas and irrigation liquid are connected to the imaging catheter via a connector 38 that connects to an irrigation/insufflation lumen of the imaging endoscope 20. In one embodiment of the invention, the irrigation and insufflation lumen are the same lumen in the imaging catheter. However, it will be appreciated that separate irrigation and insufflation lumens could be provided if desired and if space in the endoscope permits.

Figure 3B:
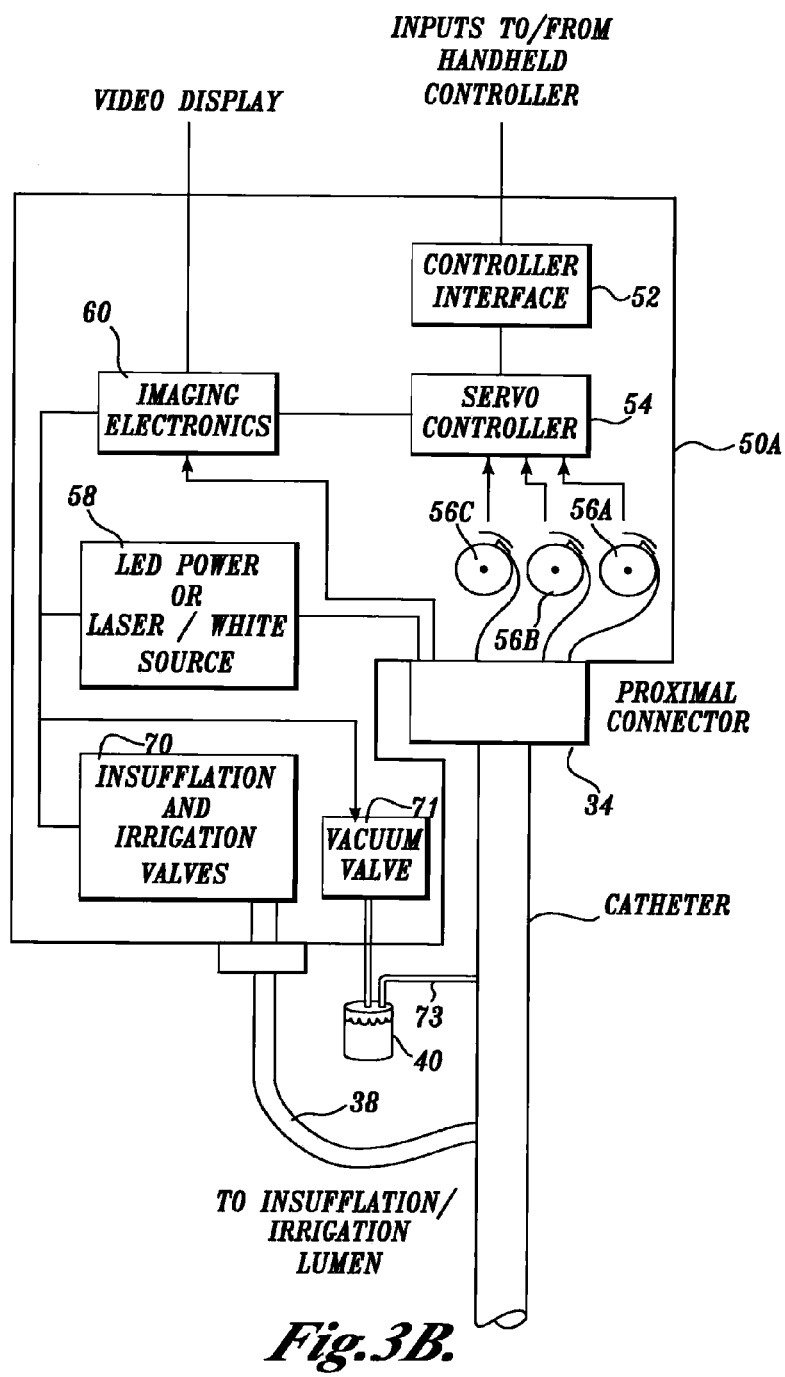
FIG. 3B is a block diagram of a motion control cabinet that interfaces with an imaging endoscope in accordance with another embodiment of the present invention.

FIG. 3B illustrates another embodiment of a motion control cabinet 50A that is similar to the cabinet shown in FIG. 3A. The motion control cabinet 50A includes a vacuum valve 71 that controls vacuum delivered to a vacuum collection bottle 40. A vacuum line 73 connects to a vacuum lumen within the imaging endoscope 20. The vacuum valve 71 is controlled from the handheld controller 80.

FIGS. 4A-4D illustrate one mechanism for securing the proximal end of the imaging endoscope to the control cabinet 50 prior to performing an endoscopic examination. The control cabinet 50 includes a connector 34A having a number of shafts 57 that are driven by the servo motors 56 shown in FIGS. 3A and 3B. Each shaft 57 is shaped to be received in a corresponding spool on which the control cables are wound. Also included in the connector 34A are connections to the insufflation and irrigation valves 70 and vacuum valve 71 to provide air, water and vacuum to the endoscope.

Figure 4A:
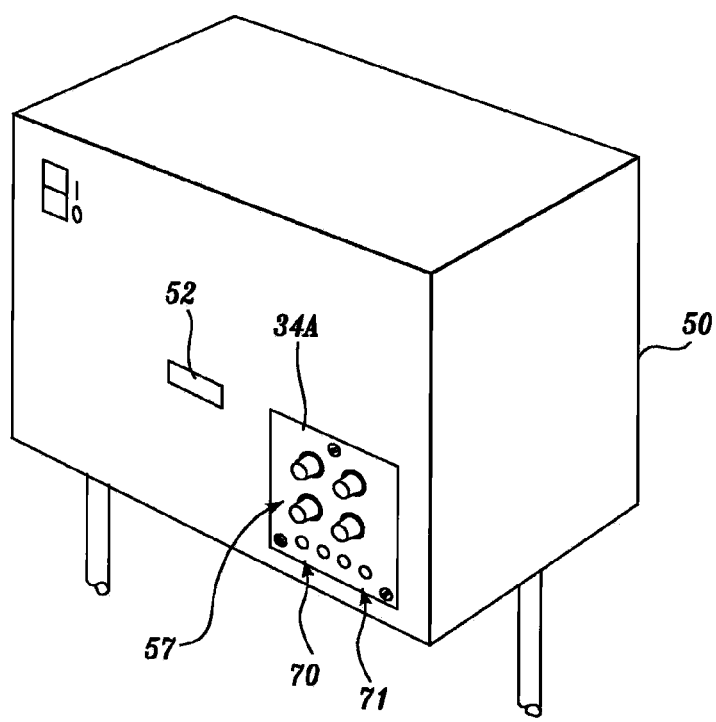
FIGS. 4A-4D illustrate one mechanism for connecting the vision endoscope to a motion control cabinet.
Figure 4B:
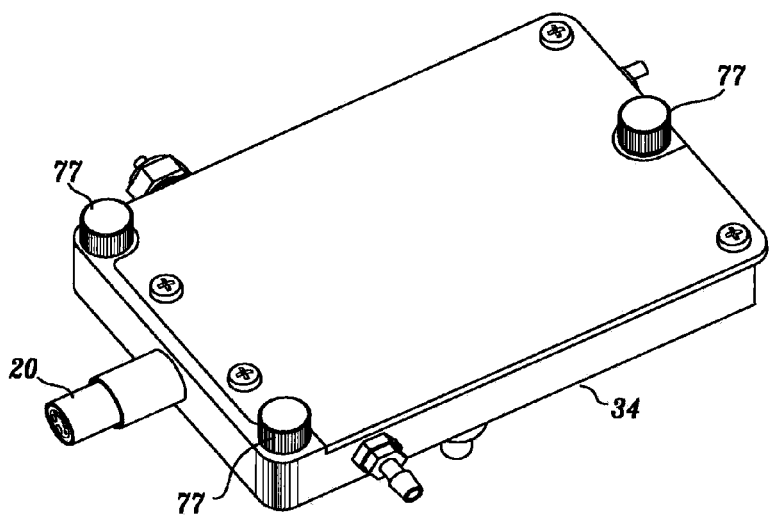
Figure 4C:
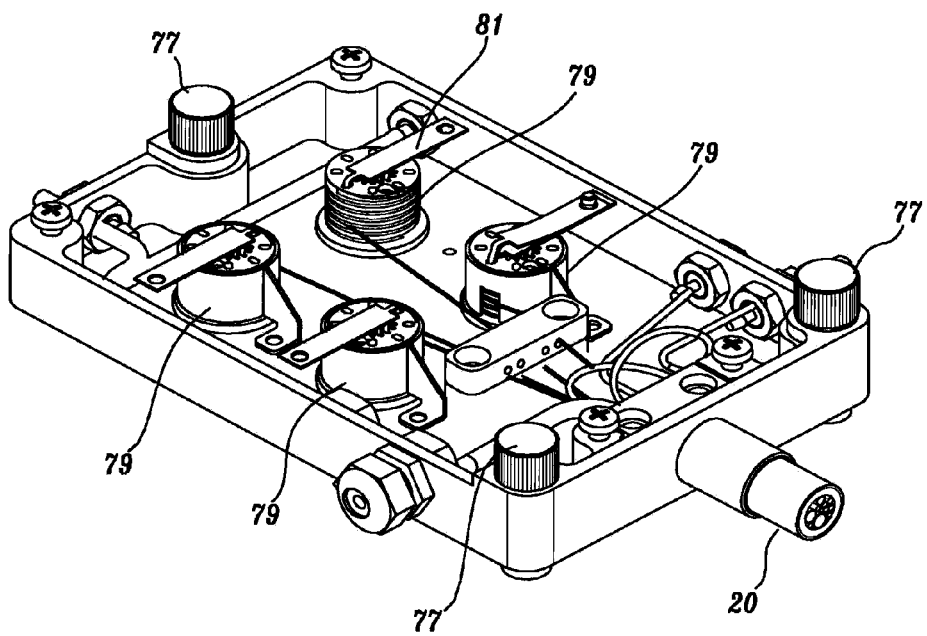

FIGS. 4A and 4B illustrate one possible connector 34 found at the proximal end of the endoscope 20 for securing the endoscope to the motion control cabinet 50. The connector 34 includes a number of thumbscrews 77 or other quick release mechanisms that allow the connector 34 to be easily secured to the connector 34A on the motion control cabinet. As shown in FIG. 4C, the connector 34A includes a number of spools 79 about which the control cables are wound. Each spool is preferably threaded or grooved to prevent the control cables from binding on the spool during use. A cover may surround a portion of the spool to keep the control cables against the spool and to aid in supporting the spool within the connector 34. In one embodiment of the invention, the spools are prevented from rotating when the connector is not engaged with the motion control cabinet 50 by brakes 81 having pins that fit within corresponding slots in the spool. Once the connector 34 is mounted to the motion control cabinet 50, the brakes 81 are disengaged from the spool such that the spool can be moved by the servo motors. Electrical connections for the light source and image sensor as well as connections to the air and water valves can be found on the sides of the connector or on the rear face of the connector 34 to engage the valves, as shown in FIG. 4A.

Figure 4D:
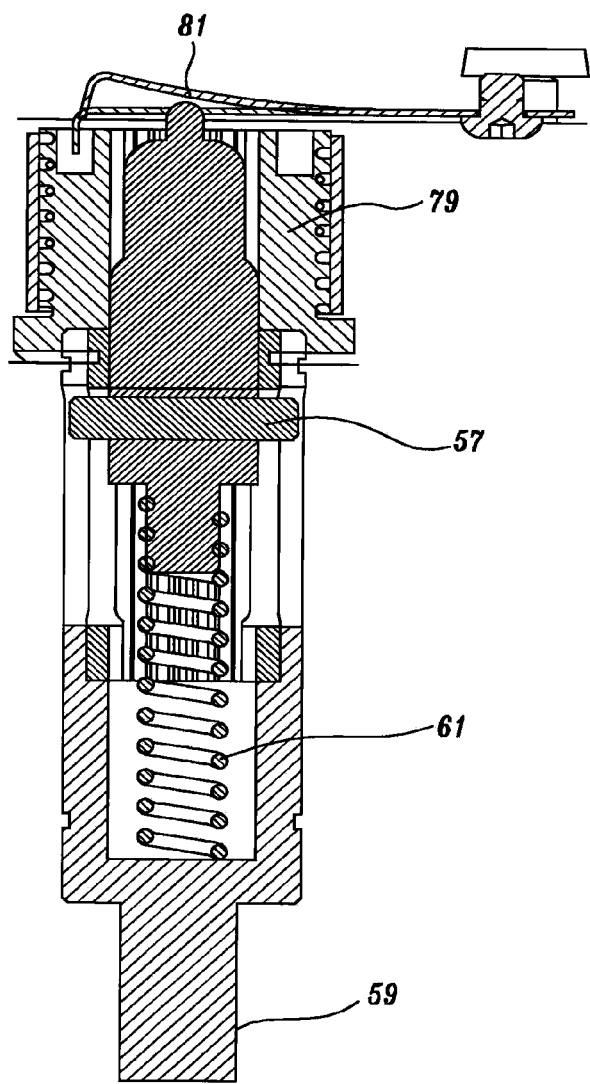

FIG. 4D illustrates a cross-sectional view of a shaft 57 fitted within a spool 79. The shaft 57 is supported by a cylinder 59 having a spring 61 therein such that the shaft 57 is free to move within the cylinder 59. The cylinder 59 is directly coupled to the servo motors within the motion control cabinet. The spring 61 allows the shaft 57 to float such that the shaft can more easily align and engage the mating surface of the spool 79.

Upon insertion of the shaft 57 into the spool 79, the brake 81 is released, thereby allowing the spool 79 to be moved by rotation of the cylinder 59. In some instances, the brake 81 may be omitted, thereby allowing the spools 79 to freely rotate when the connector 34 is not engaged with the motion control cabinet 50.

Figure 5:
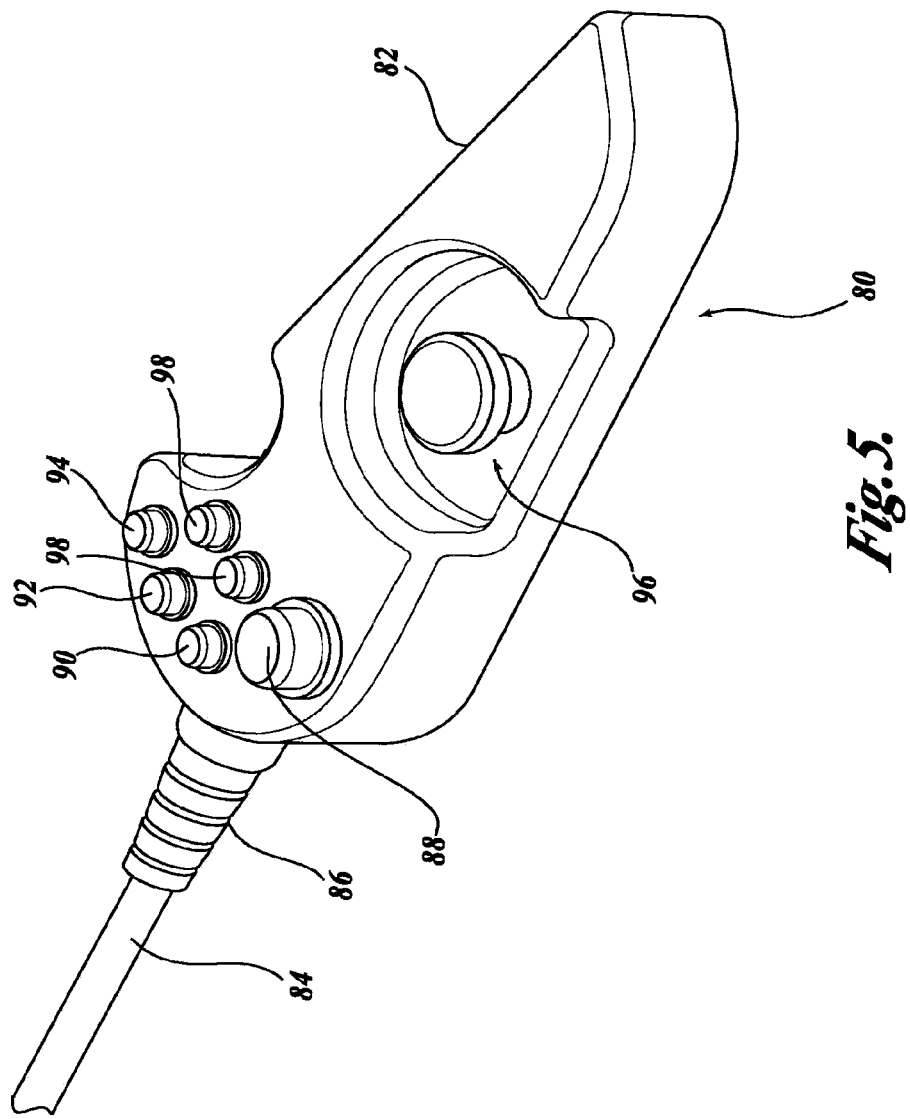
FIG. 5 is a detailed view of one embodiment of a handheld controller for controlling an imaging endoscope.

FIG. 5 illustrates various controls located on the handheld controller 80 in accordance with one embodiment of the invention. The handheld controller 80 includes a controller body 82 that, in the parallel embodiment of the invention, is coupled to the motion control cabinet 50 by an electrical cord 84, a wireless radio frequency channel, an infrared or other optical link. If the connection is made with an electrical cord, a strain relief 86 is positioned at the junction of the electrical cord 84 and the body 82 of the controller to limit the bending of the electrical wires within the electrical cord 84. In the serial embodiment of the invention, the connection of the handheld controller 80 to the motion control cabinet 50 is made with a conductor that includes both the wires to transmit signals to the motion controllers and imaging systems, as well as a lumens to carry the insufflation air/gas and irrigation liquid. In addition, the control cables of the endoscope engage cables connected to the actuators in the motion control cabinet through the handheld controller 80.

Positioned in an ergonomic arrangement on the handheld controller 80 are a number of electrical switches. An articulation joystick 88 or other multi-positional device can be moved in a number of positions to allow the physician to orient the distal tip of the imaging endoscope in a desired direction. In order to guide the imaging endoscope manually, the physician moves the joystick 88 while watching an image on a video monitor or by viewing the position of the distal tip with another medial imaging technique such as fluoroscopy. As the distal tip of the endoscope is steered by moving the joystick 88 in the desired direction, the physician can push, pull and/or twist the endoscope to guide the distal tip in the desired direction.

A camera button 90 is provided to capture an image of an internal body cavity or organ in which the imaging endoscope 20 is placed. The images collected may be still images or video images. The images may be adjusted for contrast or otherwise enhanced prior to display or storage on a recordable media.

An irrigation button 92 activates an irrigation source to supply a liquid such as water through an irrigation lumen of the imaging endoscope. The liquid serves to clean an image sensor and the light source at the distal end of the endoscope as well as an area of the body cavity. An insufflation button 94 is provided to activate the insufflation source within the motion control cabinet 50 to supply air/gas through a lumen of the catheter. The supply of the insufflation gas expands portions of the body cavity around the distal tip of the endoscope so that the physician can more easily advance the endoscope or better see the tissue in front of the endoscope.

In one embodiment of the invention, the handle 82 also includes a thumb screw 96 for securing the handheld controller 80 to the breakout box 26 as indicated above. A corresponding set of threads on a breakout box 26 receive the thumb screw 96 in order to join the two parts together. One or more additional buttons 98 may also be provided to activate additional functions such as recording or printing images, adjusting light intensity, activating a vacuum control valve, etc., if desired.

The endoscope of the present invention may also be steered automatically. Images received by the imaging electronics 60 are analyzed by a programmed processor to determine a desired direction or orientation of the distal tip of the endoscope. In the case of a colonoscopy, where the endoscope is advanced to the cecum, the processor controls the delivery of insufflation air/gas to inflate the colon, the processor then analyzes the image of the colon for a dark spot that generally marks the direction in which the scope is to be advanced. The processor then supplies control instructions to the servo controller 54 such that the distal tip is oriented in the direction of the dark spot located.

In other modes, a processor in the motion control cabinet causes the distal tip of the endoscope to move in a predefined pattern. For example, as the scope is being withdrawn, the distal tip may be caused to move in a search pattern such that all areas of a body cavity are scanned for the presence of disease. By using the automatic control of the distal tip, a physician only has to advance or retract the scope to perform an examination.

Figure 6:
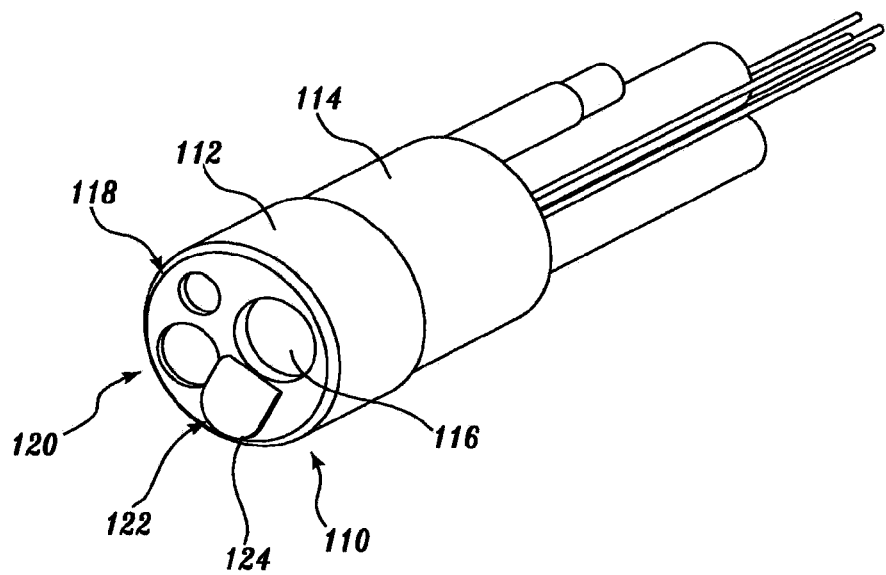
FIG. 6 illustrates one embodiment of a distal tip of an imaging endoscope in accordance with the present invention.

As will be described in further detail below, the imaging endoscope 20 generally comprises a hollow shaft having one or more lumens formed of polyethylene tubes which terminate at the distal tip 22. As shown in FIG. 6, one embodiment of a distal tip 110 comprises a cylinder having a distal section 112 and a proximal section 114. The proximal section 114 has a smaller diameter than the diameter of the distal section 112 in order to form a stepped shoulder region. The diameter of the shoulder is selected that shaft walls of the endoscope can seat on the shoulder region to form a smooth outer surface with the distal section 112. The distal face of the distal tip 110 includes a number of ports, including a camera port 116, one or more illumination ports 118, an access port or working channel lumen 120, and a directional flush port 122.

Fitted within the camera port 116 is an image sensor (not shown) that preferably comprises a CMOS imaging sensor or other solid state device and one or more glass or polymeric lenses that produce electronic signals representative of an image of the tissue in front of the camera port 116. The image sensor is preferably a low light sensitive, low noise video VGA, CMOS, color imager or higher resolution sensor such as SVGA, SXGA, or XGA. The video output of the sensor may be in any conventional format including PAL, NTSC or high definition video format.

The illumination port 118 houses one or more lenses and one or more light emitting diodes (LEDs) (not shown). The LEDs may be high intensity white light sources or may comprise colored light sources such as red, green and blue LEDs. With colored LEDs, images in different spectral bands may be obtained due to illumination with any one or more individual colors. White light images may be obtained by the simultaneous or sequential illumination of the colored LEDs and combining individual color images. As an alternative to LEDs, the light source may be external to the endoscope and the illumination light delivered to the illumination port with a fiber optic bundle.

The access port 120 is the termination point of the working channel or lumen of the endoscope 20. In the embodiment described above, the proximal end of the working channel terminates at the breakout box 26 as shown in FIG. 2. However, the working channel could terminate nearer the proximal end of the imaging catheter.

The directional flush port 122 includes a cap 124 that directs liquid supplied through an irrigation and insufflation lumen across the front face of the distal tip 110 in the direction of the camera port 116 and/or the illumination port 118. The cap 124 thereby serves to clean the camera port 116 and the illumination port 118 for a better view of the internal body cavity in which the imaging catheter is placed. In addition, the flushing liquid cleans an area of tissue surrounding the distal end of the endoscope.

Figure 7:
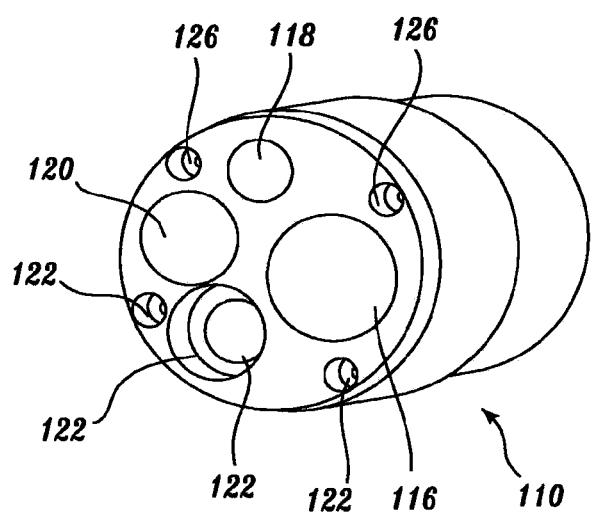
FIG. 7 illustrates one mechanism for terminating a number of control cables in a distal tip of an imaging endoscope.

FIG. 7 shows further detail of one embodiment of a distal tip 110 of the imaging endoscope. In this embodiment, the tip section 110 includes a number of counter bored holes 126 that are positioned around the circumference of the distal tip 110. The counter bored holes 126 receive swaged or flanged ends of the control cables that orient the distal tip. Tension on the control cables pull the distal tip 110 in the direction of the tensioning force.

FIG. 8 is a lengthwise, cross-sectional view of an imaging endoscope 20 in accordance with one embodiment of the present invention. The distal tip 110 is adhesively secured, welded or otherwise bonded within a center lumen at the distal end of the articulation joint 30. Secured to the proximal end of the articulation joint 30 is a distal end of a shaft 128. As discussed above, the shaft 128 is preferably stiffer or better able to transmit torque towards the distal end of the endoscope than at the proximal end of the endoscope.

The control cables 130 that move the distal tip of the endoscope are preferably made of a non-stretching material such as stainless steel or a highly oriented polyethylene-theralate (PET) string. The control cables may be routed within a center lumen of the shaft 128 or, as shown in FIG. 8, may be routed through lumens formed within the walls of the shaft. The control cables 130 extend through guides within the walls of articulation joint 30 and terminate either at the distal end of the articulation joint 30 or in the distal tip section 110.

If the control cables are routed through the center lumen of the shaft 128, the cables are preferably carried in stainless steel or plastic spiral wrapped lumens to prevent binding and a transition guide 140 such as that as shown in FIGS. 9A and 9B may be used to guide the control cables into the proximal end of the articulation joint. The transition guide 140 has a proximal end 142 that is secured within a lumen of the distal end of the shaft. A central body portion 144 of the transition guide 140 has a diameter equal to the outer diameter of the imaging endoscope. In addition, the body portion 144 includes a number of diagonal lumens 148 that extend from a center lumen of the proximal end 142 to an outer surface of a stepped distal end 146 of the transition guide. The distal end 146 is secured within a proximal end of the articulation joint 30. Control cables in the diagonally extending lumens 148 are therefore guided to the outer edge of the catheter where they extend through the guides or control cable lumens of the articulation joint 30.

FIGS. 10A, 10B illustrate one embodiment of a shaft that comprises the imaging endoscope 20. The shaft 160 has a cover 162 that may include a wire or other braid 164 embedded therein. The braid 164, if present, allows the torque characteristics of the shaft to be adjusted. The cover 162 may be formed by placing a sleeve over a mandrel. The braid 164 is placed over the sleeve and the mandrel is dipped into or sprayed with a coating material. Preferably the sleeve and coating material are made of polyurethane or other biocompatible materials such as polyethylene, polypropylene or polyvinyl alcohol. In addition, the interior lumen(s) and exterior of the shaft can be coated with a extrudable, hydrophilic, lubricious coating such as the HYDROPASS™ hydrophilic coating available from Boston Scientific, of Natick, Mass., and described in U.S. Pat. Nos. 5,702,754 and 6,048,620 which are herein incorporated by reference.

A plastic spiral wrap 166 such as spiral wire wrap available from Panduit Inc. is inserted into a lumen of the cover 162. The spiral wrap 166 prevents the shaft 160 from crushing as it is bent around a patient's anatomy.

In one embodiment of the shaft 160, the spiral wrap has a thickness of 0.060 inches and a pitch of 3/16 inch. However, it will be appreciated that other thicknesses of spiral wrap with a different pitch could be used to provide the desired column strength and bend modulus as well as to prevent kinking.

FIG. 11 shows one method of altering the torque fidelity of the distal and proximal portions of the shaft. The shaft 160 has a flexible section 170 that is proximal to the break out box and a stiffer section 172 that is distal to the break out box. The portion of the scope that is distal to the break out box has an increasing flexibility toward the distal tip and conversely a higher torque fidelity and column strength proximally To increase the torque fidelity characteristics of the distal section 172 of the shaft, a braid 164 in that section includes two or more wires that are wound in opposite directions. In one embodiment, the wire braid has a pitch of 14-16 pik. However, the number of wires and their spacing can be adjusted as needed in order to tailor the torque fidelity of the shaft.

The proximal end 170 of the shaft 160 has a single spiral of wire 176 that is preferably wound in the same direction as the plastic spiral wrap 166 in the center lumen of the shaft 160. Again, the torque fidelity of the proximal end of the shaft 170 can be adjusted by adjusting the pitch and/or direction of the wire 176 and its flexibility.

As will be appreciated, the single wire spiral 176 provides some torque fidelity but does have the same torque fidelity as the dual wire braid in the distal section of the shaft. The single wire spiral 176 may be omitted from the proximal portion of the shaft if even less torque fidelity is desired.

Figure 12A:
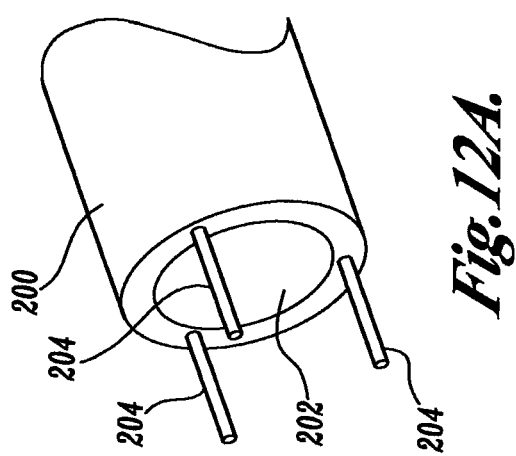
FIGS. 12A and 12B illustrate an extrusion used to make an articulation joint in accordance with one embodiment of the present invention.
Figure 12B:
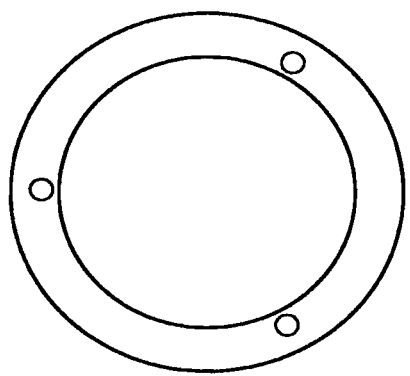

In order to facilitate steering the distal tip of imaging endoscope, the endoscope includes an articulation joint that allows the distal tip to be turned back on itself, i.e., over an arc of 180 degrees, by the control cables. As shown FIG. 12A, 12B[,?] an articulation joint 200 is formed from a cylinder of a plastically deformable material having a central lumen 202, and a number of control wire lumens 204 located in the walls of the articulation joint. If desired, the space between the control wire lumens in the cylinder wall may be thinner such that the control wire lumens form bosses that extend into the central lumen of the cylinder. The control cable lumens 204 are preferably oriented at 120° apart if three control cables are used or 90° apart if four control cables are used.

Figure 13:
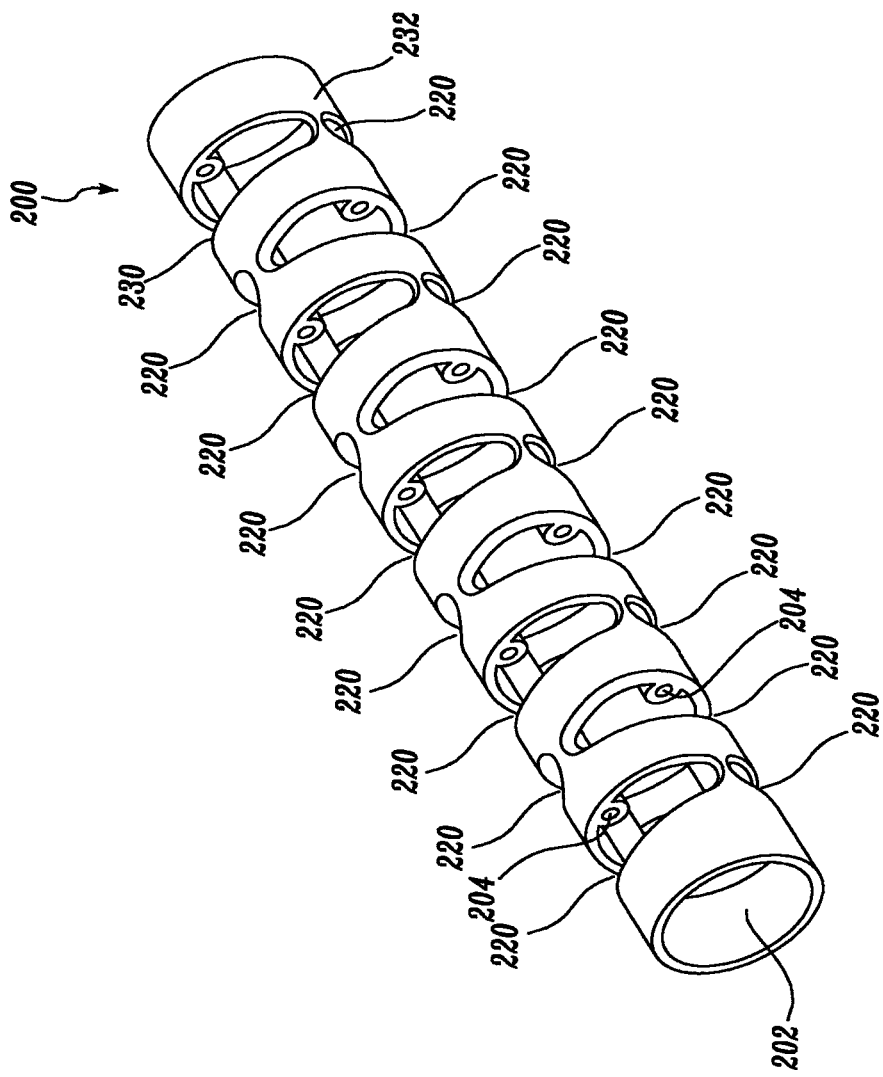
FIG. 13 illustrates an articulation joint in accordance with one embodiment of the present invention.

To facilitate bending of the articulation joint, the cylinder includes a number of live hinges 220 formed along its length. As can be seen in FIG. 13, each live hinge 220 comprises a pair of opposing V-shaped cuts 230 on either side of the cylinder and are separated by a flexible web 232 that forms the bendable portion of the hinge. In the embodiment designed for four control cables, each live hinge is oriented at 90 degrees with respect to an adjacent hinge.

Upon retraction of a control cable, those live hinges having webs 232 that are in line with the retracting control cable do not bend. Those live hinges having webs that are not in line with the control cable will be closed, thereby bending the articulation joint in the direction of the control cable under tension.

Another advantage of the articulation joint shown in FIG. 13 is that the distal end of the scope can be retracted by pulling all the control cables simultaneously. This allows the physician to maneuver the distal tip in the body without having to move the remaining length of the endoscope. This may be useful when performing surgical procedures such as obtaining a biopsy or snaring polyps.

The articulation joint can be formed by extruding a cylinder with the central and control cable lumens in place and cutting the cylinder tube with a knife, laser, water jet, or other material removal mechanism to form the live hinges. Alternatively, the articulation joint can be molded with the live hinge joints in place. As will be appreciated, the angles of the V-shaped cuts that form the hinges may be uniform or may vary along the length of the articulation joint. Similarly, the distance between adjacent live hinges may be uniform or may vary in order to tailor the bending and torque fidelity characteristics of the articulation joint. In one embodiment of the invention, each live hinge has a closing angle of 30° so that six hinges are required to provide 180° of movement. The distal end of the articulation joint 200 may be counter-bored to receive the distal tip section 110 of the endoscope, as discussed above. Similarly, the proximal end of the articulation joint 200 is adapted to receive the distal end of the shaft of the endoscope. In the embodiment shown in FIG. 13, the control cable lumens 204 are aligned with the widest spacing of the live hinges and with the web portion of each hinge. However, it may be desirable to offset the control cable lumens 204 with respect to the hinges in order to lessen potential binding of the control cables in the hinge. As indicated above, the articulation joint should be made of a biocompatible material that will bend but will not collapse. Suitable materials include polyurethane, polyethylene, polypropylene, or other biocompatible polymers.

Figure 15:
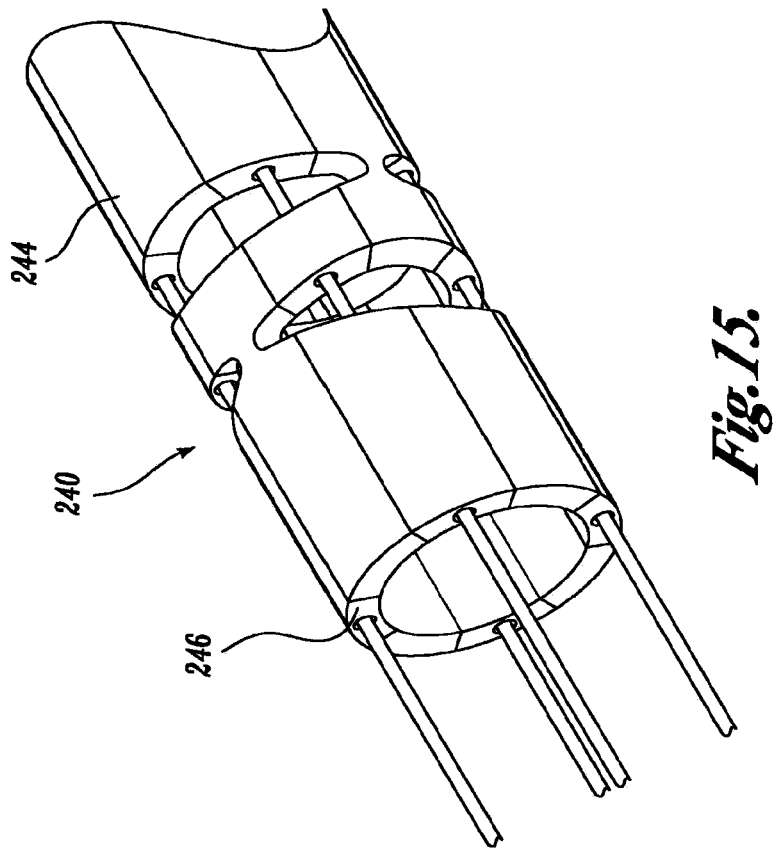
FIGS. 14 and 15 illustrate an extrusion having areas of a different durometer that is used to form an articulation joint in accordance with another embodiment of the present invention.
Figure 14:
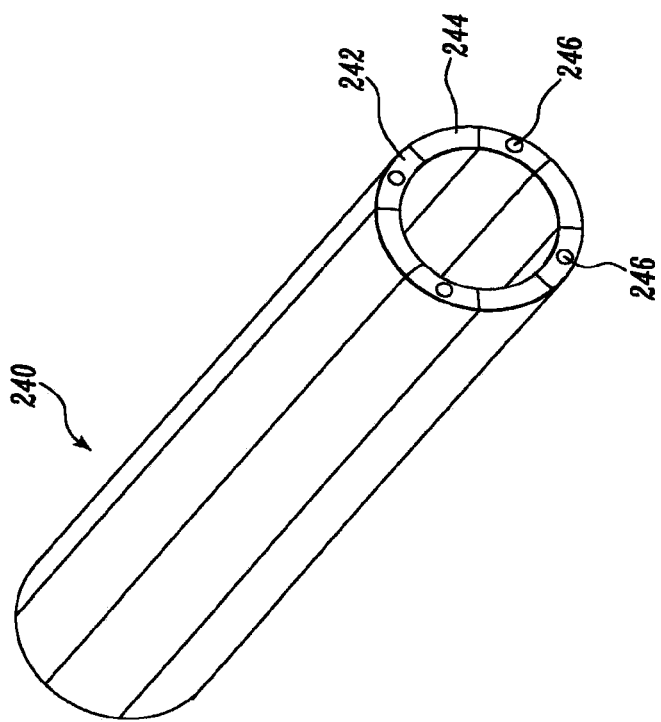

To prevent wear by the control cables as they are pulled by the actuation mechanism in the motion control cabinet, it may be desirable to produce the articulation joint from a material having areas of different durometers. As shown in FIGS. 14 and 15, a cylinder formed from an extruded tube 240 has alternating bands of a high durometer material 242 and a lower durometer material 244 around its circumference. The lumens 246 used to route the control cables are formed in the high durometer material to resist abrasion as the control cables are tensioned and released. In addition, the high durometer material also reduces friction between the control cables and the surrounding lumen. FIG. 15 illustrates an articulation joint where the control cable lumens are offset with respect to the orientation of the web portions 248 of the live hinges so that the control cables do not pass through the web portion of the hinge.

Figure 16A:
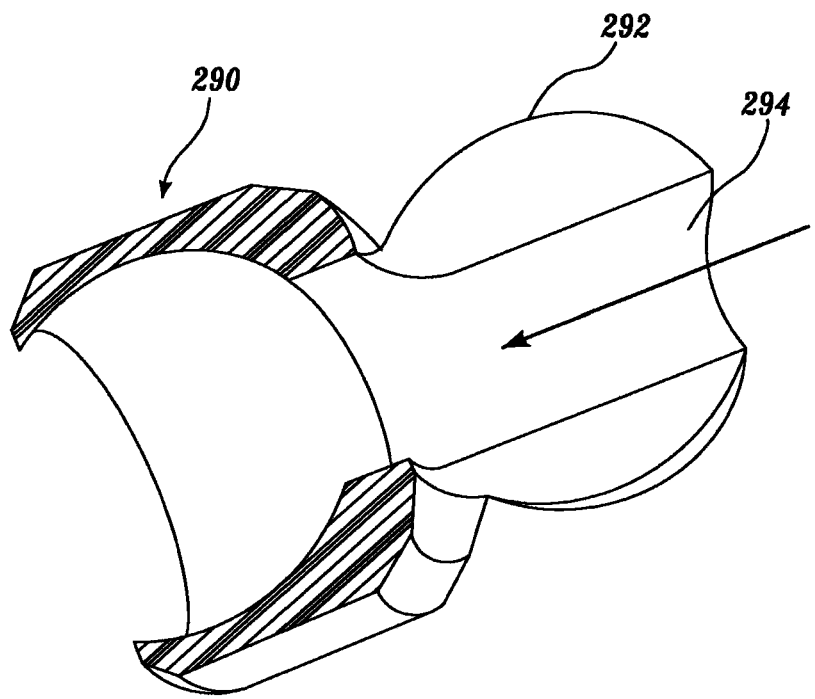
FIGS. 16A and 16B illustrate another embodiment of an articulation joint including a number of ball and socket sections.
Figure 16B:
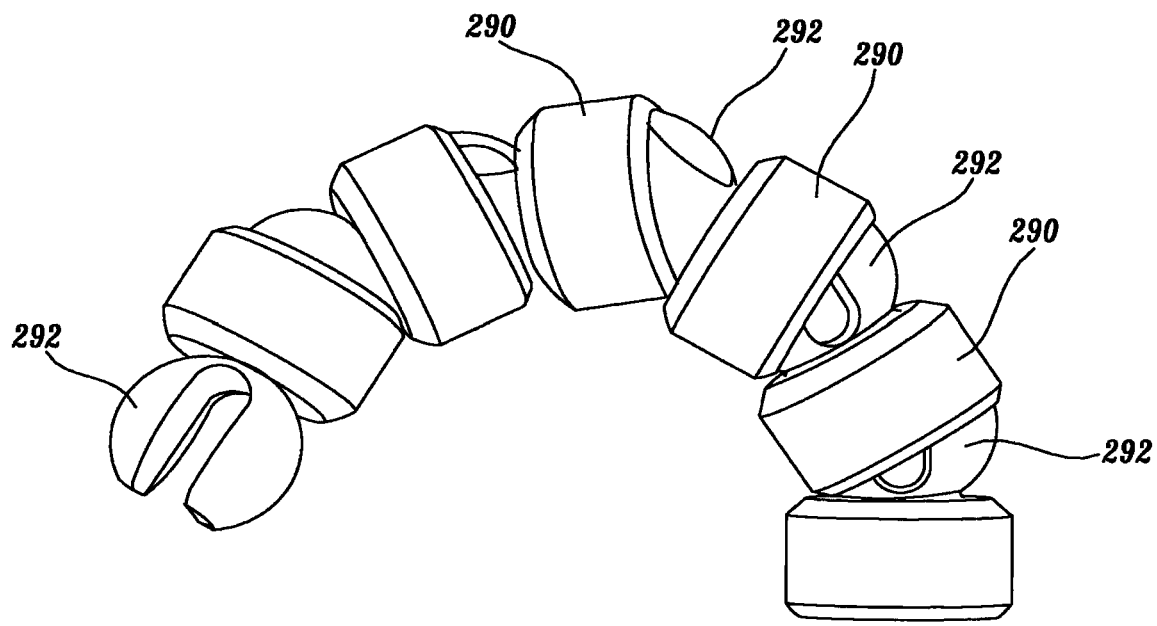

FIGS. 16A, 16B illustrate an alternative embodiment of an articulation joint. In this embodiment, the joint comprises a series of ball and socket connectors that are linked together. As shown in FIG. 16A, each connector includes a socket section 290 and a ball section 292. The ball section 292 fits in a socket section 290 of an adjacent connector. A lumen 294 extends axially through the ball section 292 to allow for passage of the wires that connect to the light source and the image sensor and tubes that carry irrigation fluids and insufflation gases. The ball and socket sections are preferably molded of a biocompatible polymer.

Figure 17B:
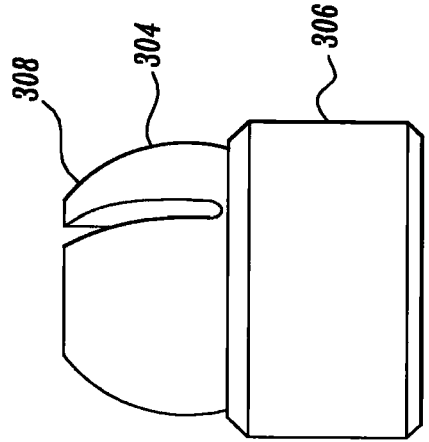
FIGS. 17A-17D illustrate various possible configurations of ball and socket sections used to construct an articulation joint.
Figure 17D:
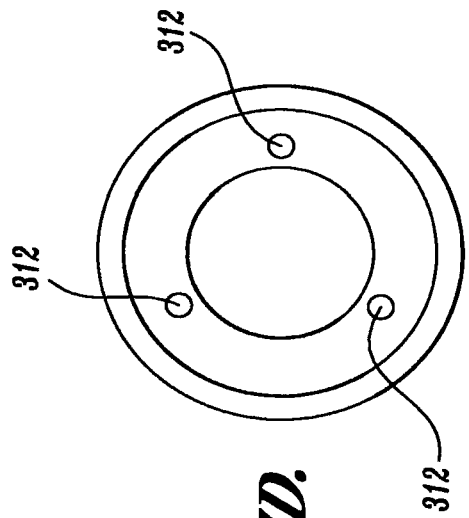
Figure 17A:
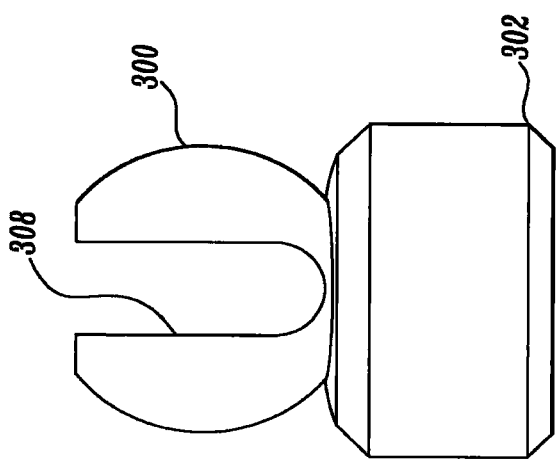
Figure 17C:
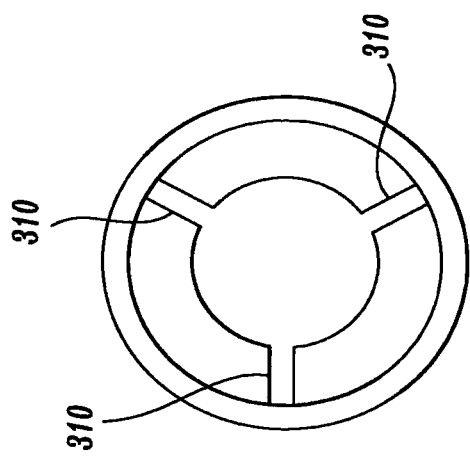

Each socket section can be formed with a fully formed ball section such as ball section 300 shown in FIG. 17A. Alternatively, a partial ball section such as ball section 304 can be formed on a socket section 306 as shown in FIG. 17B. To provide room for the control cables to move, the ball section can include slot 308 as shown in FIGS. 17A, 17B that cuts through the middle and sides of the ball section. Alternatively, a number of smaller slots 310 can be positioned around the circumference of the ball section as shown in FIGS. 17C and 17D. The slots allow the control cables to be shortened under tension. A number of holes 312 at the interface of the ball section and socket section allows passage of the control cables from the socket section into the ball section as shown in FIG. 17D.

In another embodiment of an articulation joint, the joint is made of a series of stacked discs that are positioned adjacent one another and move with respect to each other. As shown in FIG. 18A, a disc 350 comprises an annular ring 352 having a pair of rearward facing rocker surfaces or cams 354 and a pair of forward facing rocker surfaces or cams 356. The cams 354 are positioned 180° apart on the rear surface of the annular ring 352, while the forward facing cams 356 are positioned 180 degrees apart on the forward face of the annular ring 352. In the embodiment shown, the forward cams 356 are oriented at 90° with respect to the rear cams 354. Opposite each cam on the other side of the annular ring is a flat land section so that the cams of an adjacent disc may engage with and rock on the flat section. Holes 360 are drilled through the annular ring and through the cams for passage of the control cables. Upon tension of the control cables, the discs will rock on the surface of the cams 354, 356 thereby bending the articulation joint in the desired direction.

FIG. 18B shows an articulation joint made up of a series of stacked discs 350a, 350b, 350c . . . engaged with one another to form an articulation joint. A number of control cables 370a, 370b, 370c, 370d, pass through the discs and are used to pull the discs on the cam surfaces to move the joint in the desired direction.

FIGS. 19A and 19B show an alternative embodiment of the articulation joint shown in FIGS. 18A and 18B. In this embodiment, an articulation joint comprises a series of stacked discs 380, each comprising an annular ring having a pair of concave pockets 382 on its rear surface and a pair of correspondingly shaped convex cams 384 on its front surface. The concave pockets 382 are oriented at 90° with respect to the convex cams 384 so that adjacent discs may be stacked such that the cams of a disc fit within the pockets of the adjacent disc. The corresponding shaped cams 384 and pockets 382 help prevent the discs from rotating with respect to one another. Holes or lumens 386 are formed through the annular ring 380 for passage of a number of control cables 390a, 390b, 390c, 390d, as shown in FIG. 19B. The holes or lumens 386 may be positioned at the center of the cams and pockets. However, the holes for the control cables may be offset from the position of the cams and pockets, if desired. Preferably discs 380 are molded from a biocompatible polymer having a relatively slick surface, such as polyurethane, polypropylene, or polyethylene, that reduces friction between adjacent cams and pockets.

Figure 20A:
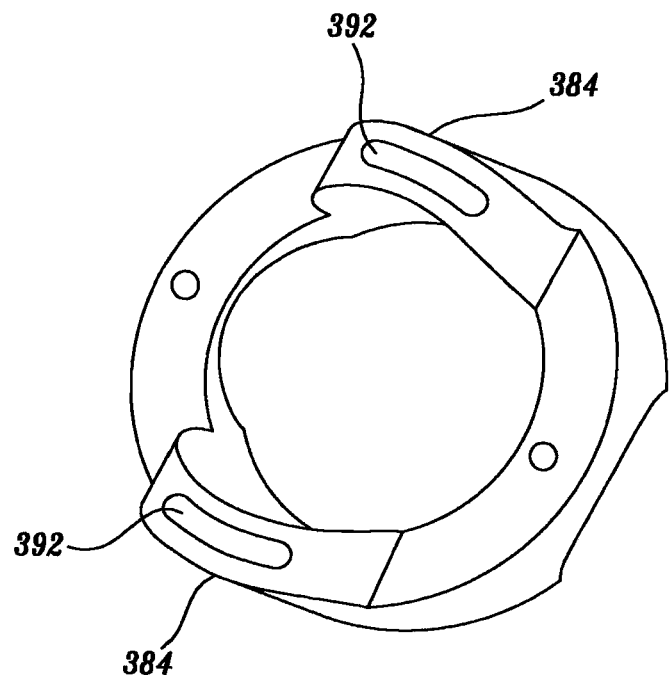
FIGS. 20A-20B illustrate a disc used to form an articulation joint in accordance with another embodiment of the present invention.
Figure 20B:
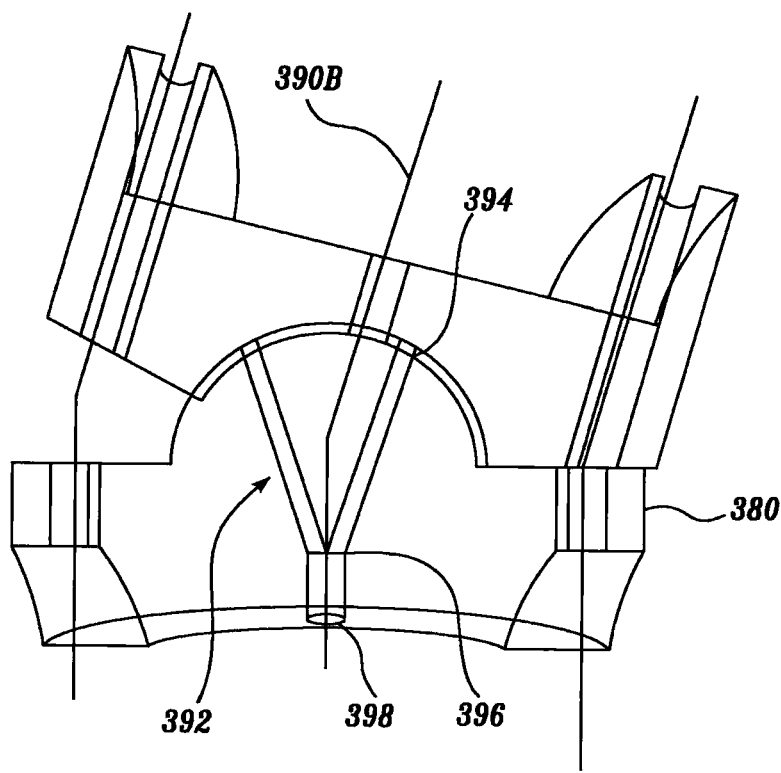

FIGS. 20A and 20B show yet another alternative embodiment of an articulation joint. In this embodiment, the articulation joint is formed of a stack of discs, each of which comprises an annular ring. The annular ring has cams having an arcuate slot 392 molded therein that allows a control cable to move more freely in the cam as the disc is moved relative to an adjacent disc. As best shown in FIG. 20B, the slot 392 tapers from a widest point 394 at the outer edge of the cam to a narrow point 396 where the slot forms a cylindrical hole 398 that extends to the opposite edge of the annular ring 380. A control wire 390*b* is free to bend within the widened portion of the arcuate slot 392 as an adjacent disc is rotated.

Although the discs of the articulation joints shown in FIGS. 18-20 are generally circular in shape, it will be appreciated that other shapes could be used. FIGS. 21A and 21B show an articulation joint formed from a number of sections having a generally square outer shape. As shown in FIG. 21A, a section 400 is a square band having a pair of pins 402 that extend outwardly on opposite sides of the rear surface of the square section. On the opposite sides of the front surface are a pair of opposing circular recesses 404 that are sized to receive the round pins 402 of an adjacent section. The embodiment shown, the control cables are routed through holes or lumens in corner blocks 406 that are found in each corner of the square section 400. FIG. 21B shows two adjacent square sections 400*a*, 400*b* secured together. As can be seen, the section 400*b* can rotate up or down on its pins with respect to the adjacent section 400*a*. Although circular and square articulation sections have been shown, it will be appreciated that other segment shapes such as triangular or pentagonal, etc., could also be used to form an articulation joint.

In some environments, a full 180° turning radius of the distal tip of the imaging endoscope may not be necessary. In those environments, the articulation joint may be replaced with a flexible member such as a braided stent. FIG. 22 shows an imaging endoscope 425 having a braided stent 430 as the articulation joint. The braided stent extends between a distal tip 432 and a connector 434 that joins the proximal end of the stent 430 with the distal end of a flexible shaft 436. A cover 438 extends over the flexible shaft 436 and the braided stent 430. Control cables (not shown) extend through a lumen of flexible shaft 436 and are used to pull the stent 430 such that the distal tip 432 is oriented in the desired direction. In addition, pulling all the control cables simultaneously allows the distal tip of the endoscope to be retracted.

FIG. 23 shows one method of securing the distal ends of the control cables to a braided stent 430. The control cables 440*a*, 440*b*, 440*c*, 440*d* can be woven through the wires of the stent 430 and terminated by forming loops around the wires that comprise the stent. Alternatively, the ends of the cables 440 can be soldered or adhesively secured to the wires of the stent.

In some embodiments, the articulation joint is designed to exert a restoring force so that imaging endoscope will tend to straighten upon the release of tension from the control cables. In other cases, it may be desirable to maintain the position of the distal tip in a certain direction. In that case, a construction as shown in FIG. 24 can be used. Here, the shaft of the imaging endoscope includes an inner sleeve 450 that is overlaid with two or more plastic spiral wraps 452, 454, and 456. Wrap 452 is wound in the clockwise direction while wrap 454 is wound in the counter-clockwise direction over the wrap 452 and the wrap 456 is wound in the same direction as the first wrap 452. The wraps are formed of a relatively coarse plastic material such that friction is created between the alternatingly wound layers of the wrap. A suitable material for the plastic wrap includes a braided polyester or polyurethane ribbon. Upon tension of the imaging endoscope by any of the control cables, the plastic spiral wraps will move with respect to each other and the friction between the overlapping wraps will tend to maintain the orientation of the imaging endoscope in the desired direction. The endoscope will remain in the desired direction until it is pulled in a different direction by the control cables. Covering the alternatingly wound spiral wraps 452, 454, and 456 is a braid 458. The braid is formed of one or more plastic or wire threads wound in alternate directions. An outer sleeve 460 covers the braid 458 to complete the shaft.

FIG. 25 shows another alternative embodiment of a shaft construction used in an imaging endoscope according to the present invention. The shaft includes a cover sheath 470 having bands of a high durometer material 472 and a low durometer material 474 that alternate around the circumference of the sheath 470. The high durometer material and low durometer materials form longitudinal strips that extend along the length of the shaft. Within the sheath 470 is a plastic spiral wrap 474 that prevents the shaft 470 from crushing as it is bent in a patient's anatomy. The high durometer materials add to the torque fidelity characteristics of the shaft. The width of the high durometer material strips compared to the low durometer material may be adjusted in accordance with the torque fidelity characteristics desired.

Figure 26:
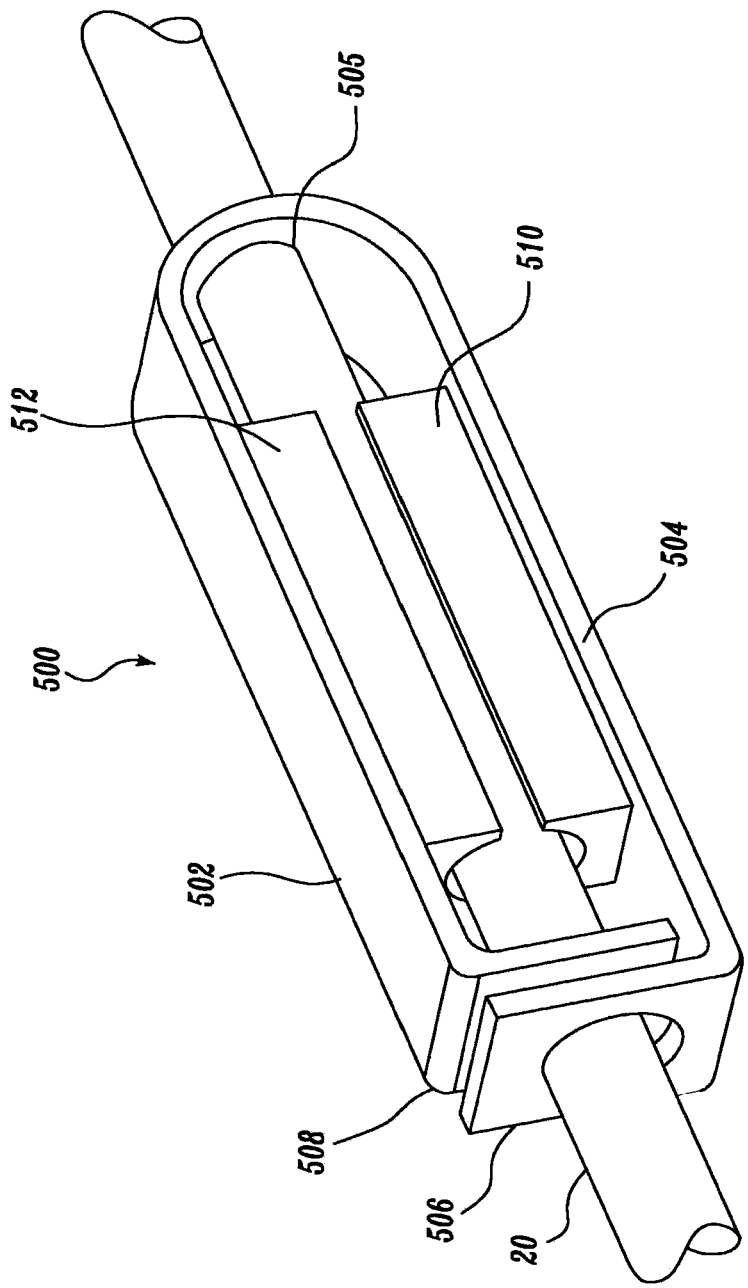
FIGS. 26-29 illustrate alternative embodiments of a gripping mechanism that rotates an imaging endoscope shaft in accordance with the present invention.

During examination with the imaging endoscope, the physician may need to twist the scope in order to guide it in the desired direction. Because the outer surface of the scope is preferably coated with a lubricant and it is round, it can be difficult for the physician to maintain an adequate purchase on the shaft in order to rotate it. As such, the imaging endoscope of the present invention may include a gripper mechanism that aids the physician in grasping the shaft for either rotating it or moving the shaft longitudinally. One embodiment of a shaft gripping device is shown in FIG. 26. Here, a gripper 500 comprises a u-shaped member having a pair of legs 502, 504 that are aligned with the longitudinal axis of an imaging endoscope 20. At the distal end of the legs 502, 504 are two 90° bends 506, 508. The gripper 500 includes a hole 505 positioned at the curved bent portion of the gripper that joins the legs as well as holes in each of the 90° sections 506, 508. The imaging endoscope passes through the holes such that the gripper 500 is slideable along the length of the shaft portion of the endoscope. The spring nature of the material used to fashion the gripper causes the legs 502, 504 to be biased away from the shaft of the endoscope. Only the friction of the opposing holes at the bent portions 506, 508 prevent the gripper 500 from freely sliding along the length of the shaft. On the inner surface of the legs 502, 504 are a pair of touch pads 510, 512, having an inner surface that is shaped to match the outer circumference of the shaft portion of the endoscope. When the physician squeezes the legs 502, 504 radially inward, the touch pads 510, 512 engage the shaft such that the physician can push or pull the endoscope or rotate it. Upon release of the legs 502, 504, the touch pads 510, 512 release from the surface of the shaft and the gripper 500 can be moved along the length of the shaft to another location if desired.

Figure 27:
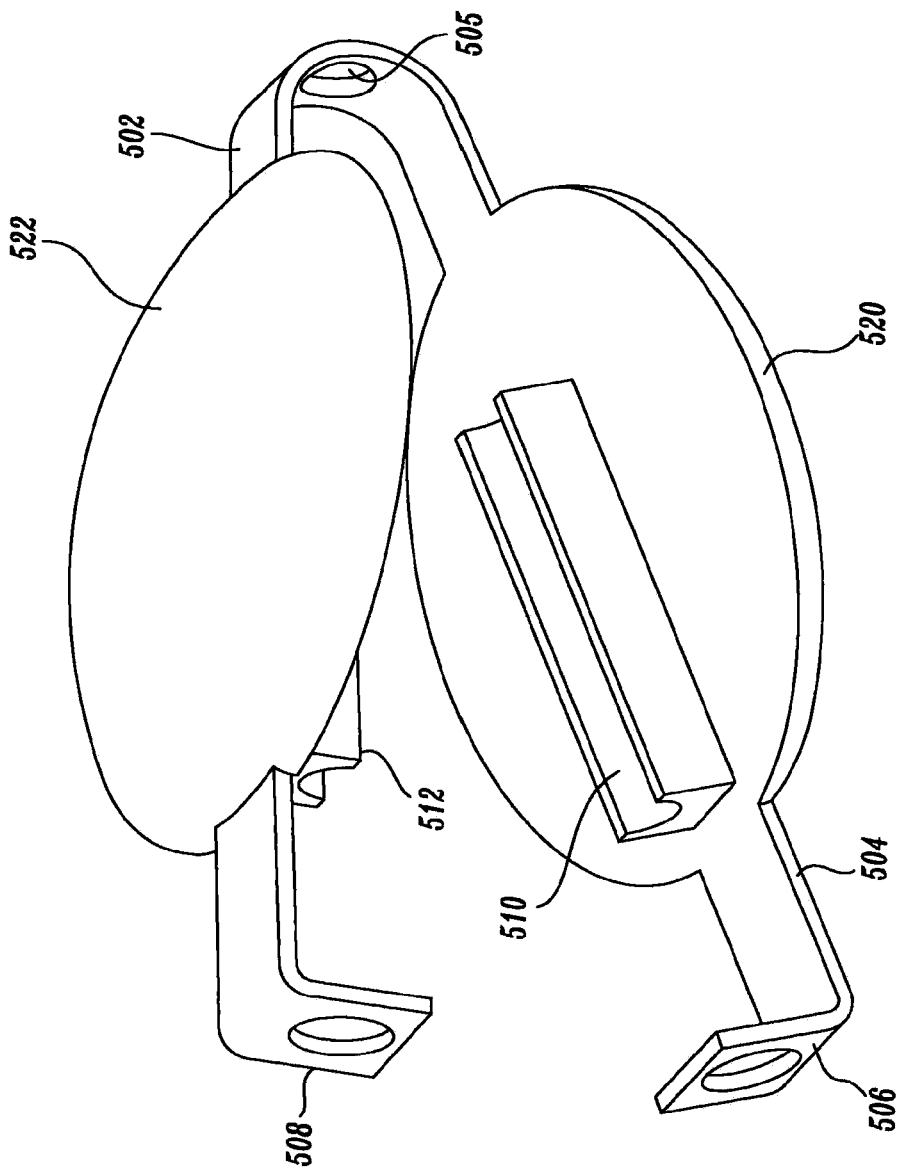

FIG. 27 shows a gripper similar to that of FIG. 26 with like parts being identified with the same reference numbers. In this embodiment, the gripper includes two hemispherical discs 520, 522, positioned on the outside surface of the legs 502, 504. The hemispherical surfaces 520, 522 are designed to fit within the hand of the physician and increase the radial distance from the gripper to the shaft such that it is easier to twist the shaft, if desired.

Figure 28:
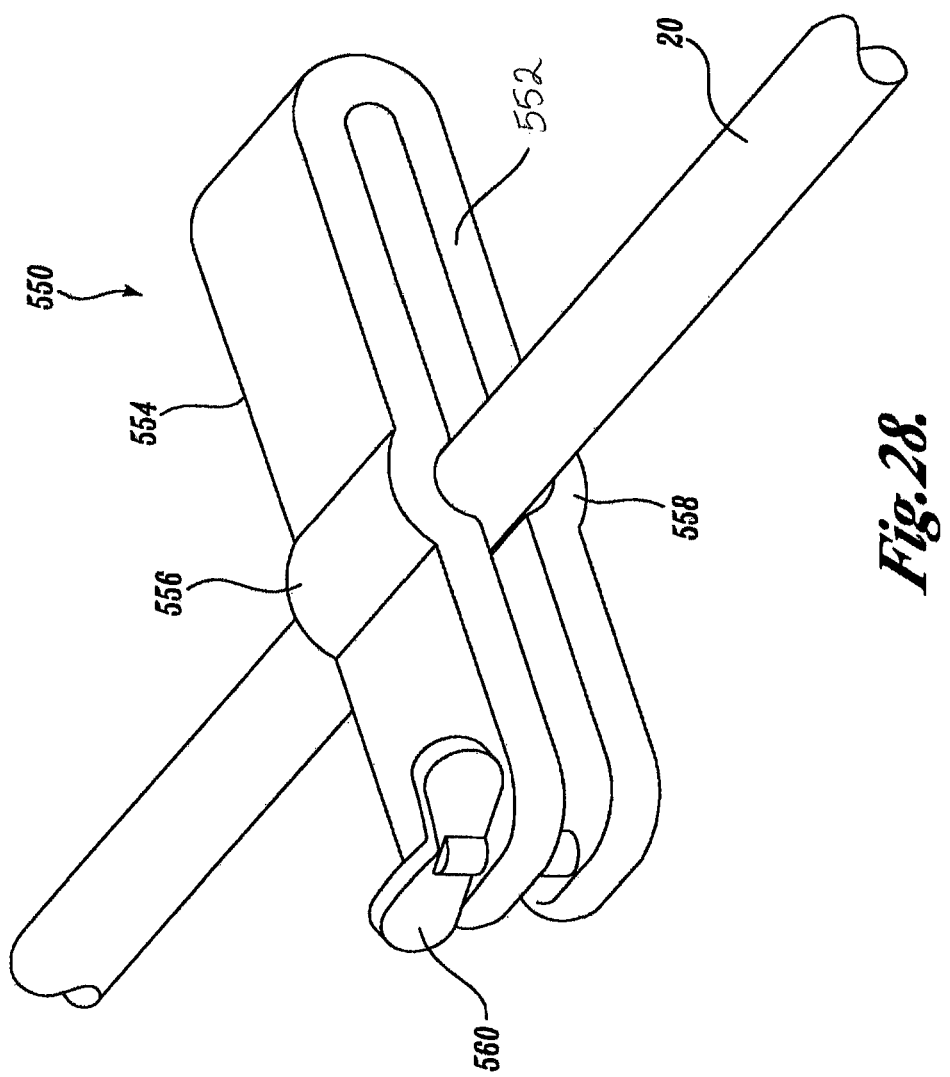

FIG. 28 shows yet another alternative embodiment of a shaft gripper. In this example, a gripper 550 comprises a u-shaped member having a pair of legs 552, 554, that are oriented perpendicularly to the longitudinal axis of the imaging endoscope 20. The legs 552, 554 include a recessed section 556, 558 that is shaped to receive the outer diameter of the shaft portion of the endoscope. A thumbscrew 560 is positioned at the distal end of the legs such that the legs can be drawn together and cause the legs 554, 556 to securely engage the shaft of the endoscope. Upon release of the thumbscrew 560, the legs 554, 552 are biased away from the shaft such that the gripper 550 can be moved. The shaft can be twisted by rotating the legs 552, 554, with respect to the longitudinal axis of the shaft.

Figure 29:
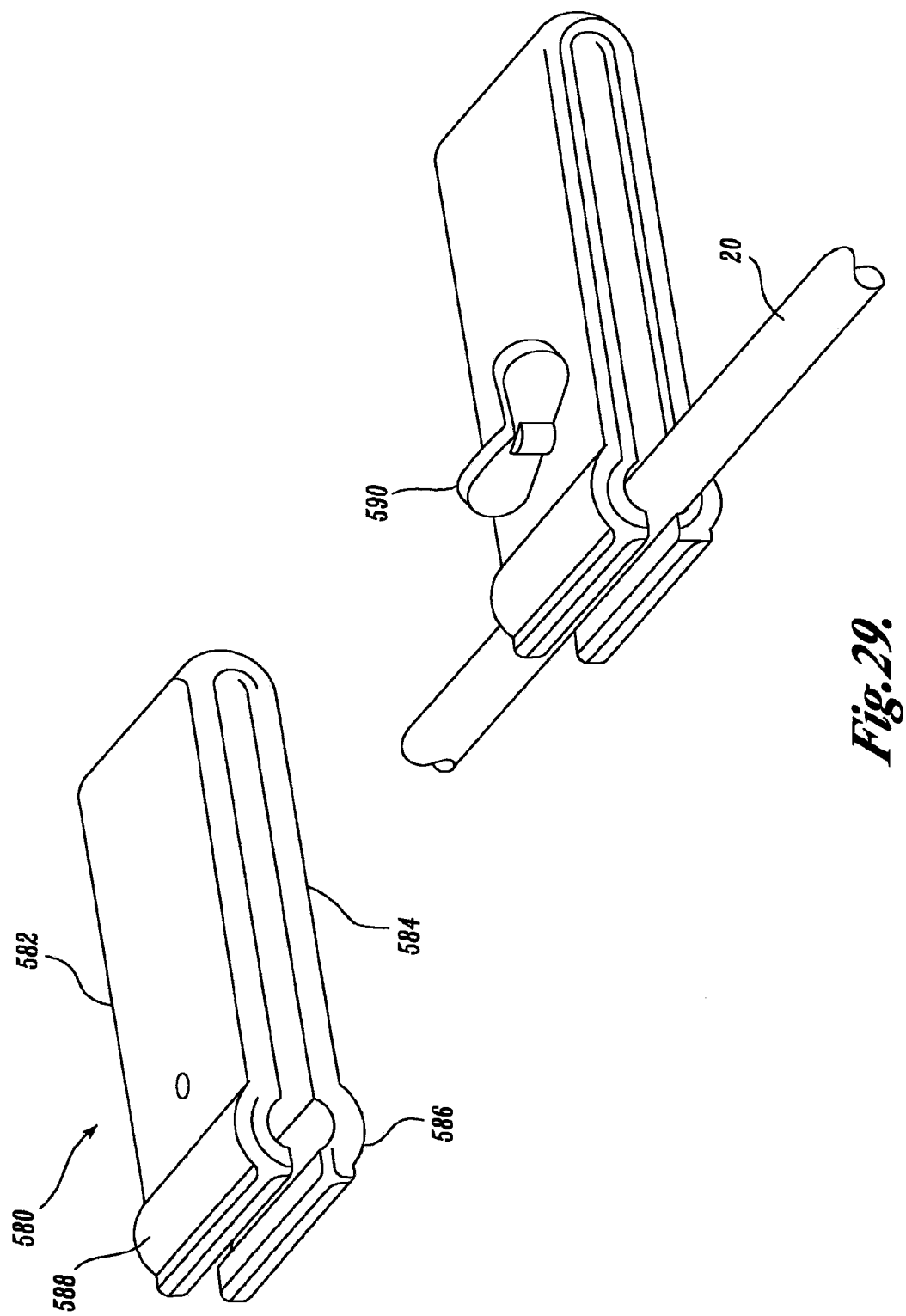

FIG. 29 shows an alternative embodiment of the gripper 550 shown in FIG. 28. In this example, the gripper 580 includes a u-shaped member having a pair of legs 582, 584. At the distal end of each leg is a recess 586, 588 that is shaped to receive the outer diameter of the shaft. The shaft is placed in the recesses 586, 588, and a thumbscrew is positioned between the ends of the legs 582, 584, and the u-shaped bend in the gripper 580. By tightening the thumbscrew 590, the legs are compressed against the shaft of the imaging endoscope 20, thereby allowing the physician to rotate the endoscope by moving the gripper 580.

In one embodiment of the invention the endoscope has a movable sleeve that operates to keep the distal end of the endoscope clean prior to use and covers the end of the scope that was in contact with a patient after the scope has been used.

FIGS. 30A and 30B illustrate one embodiment of an endoscope 594 having a sponge 504 at its distal end. The sponge fits over the endoscope and has a peel off wrapper that may be removed and water or other liquid can be applied to the sponge. The water activates a hydrophilic coating so that the distal end of the endoscope has an increased lubricity. In addition, the sponge functions as a gripper when compressed allowing the physician to pull and/or twist the endoscope.

A collapsible sleeve 598 is positioned over the distal end of the endoscope and can be retracted to expose the lubricated distal tip of the probe. In one embodiment, the sleeve 598 is secured at its distal end to the sponge 594 and at its proximal end to the breakout box. Moving the sponge proximally retracts the sleeve so that the endoscope is ready for use. After a procedure, the sponge 594 is moved distally to extend the sleeve over the distal end of the endoscope. With the sleeve extended, any contaminants on the probe are less likely to contact the patient, the physician or staff performing the procedure.

Figure 31:
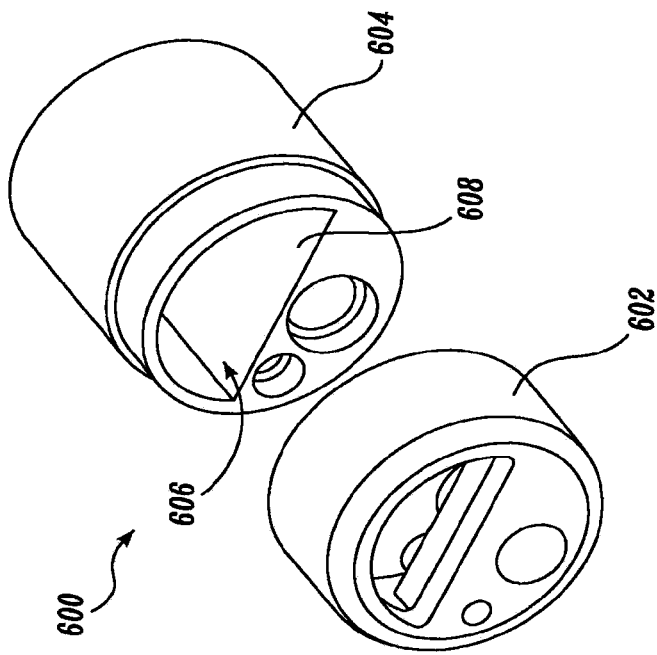
FIG. 31 illustrates one embodiment of a heat dissipating distal tip of an endoscope in accordance with the present invention.

In some instances, it may be desirable to limit the amount of heat that is dissipated at the distal end of the imaging endoscope. If light emitting diodes are used, they generate heat in the process of producing light for illumination. Similarly, the image sensor generates some heat during operation. In order to limit how hot the distal end of the endoscope may become and/or to provide for increased life for these components, it is necessary to dissipate the heat. One technique for doing so is to fashion a heat sink at the distal tip of the imaging endoscope. As shown in FIG. 31, a distal tip 600 includes a cap 602 and a heat dissipating section 604 that is made of a heat dissipating material such as a biocompatible metal. The heat dissipating section 604 includes a semicircular opening 606 having a relatively flat base 608 that extends approximately along the diameter of the heat dissipating section 604.

The flat base 608 forms a pad upon which electrical components such as the LEDs and image sensor can be mounted with a thermally conductive adhesive or other thermally conductive material. The heat generating devices will transfer heat generated during operation to the heat dissipating section 604. The distal cover 602 covers the distal end of the heat dissipating section 604 in order to prevent the heat dissipating section 604 from touching the tissue in the body as well as to protect the body as the imaging catheter is moved in the patient. Prisms, lenses, or other light bending devices may be needed to bend light entering the distal end of the endoscope to any imaging electronics that are secured to the relatively flat base 608 of the heat dissipating section 604.

Figure 32:
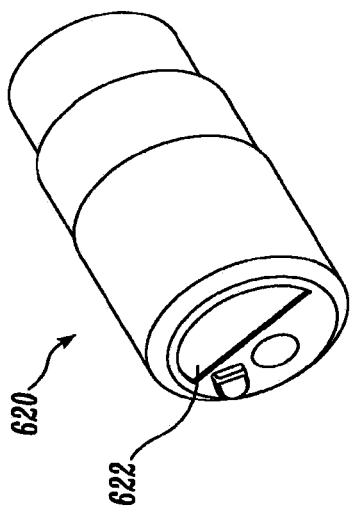

FIG. 32 shows a heat dissipating distal tip of an endoscope wherein the distal tip does not include a cover but is molded from a single piece of heat dissipating material such as a biocompatible metal. The heat dissipating section 620 again includes a semicircular opening with a relatively flat surface 622 that extends along the diameter of the section and on which heat generating electronic devices can be mounted. With a semicircular opening formed in the distal end of the heat dissipating distal tip 620, the illumination mechanism and image sensor are mounted on the flat surface 622. The irrigation port is oriented to direct water over the hemispherical cutout in order to clean the illumination mechanism and image sensor or image sensor lenses.

In yet another embodiment of the invention, the imaging devices at the distal end of the endoscope can be cooled by air or water passed through a lumen to the end of the endoscope and vented outside the body. For example, air under pressure may be vented through an orifice near the imaging electronics. The expansion of the air lowers its temperature where it cools the imaging electronics. The warmed air is then forced to the proximal end of the endoscope through an exhaust lumen. Alternatively, the endoscope may include a water delivery lumen that delivers water to a heat exchanger at the distal tip. Water warmed by the electronic components in the distal tip is removed in a water return lumen.

Figure 33:
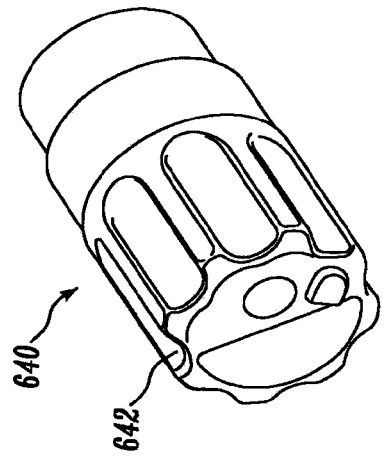
FIGS. 32 and 33 illustrate alternative embodiments of a heat dissipating distal tip in accordance with the present invention.

FIG. 33 shows an alternative embodiment of the heat dissipating distal tip shown in FIG. 31. In this example, the heat dissipating distal tip 640 has a number of scalloped channels 642 positioned around the circumference of the distal tip. The scalloped channels 642 increase the surface area of the heat dissipating distal tip, thereby further increasing the ability of the tip to dissipate heat from the illumination and imaging electronic devices.

Although the present endoscopic imaging system has many uses, it is particularly suited for performing colonoscopic examinations. In one embodiment, a 10-13 mm diameter prototype having a 0.060 inner spiral wrap with a pitch of ¼ inch and coated with a hydrophilic coating was found to have a coefficient of friction of 0.15 compared to 0.85 for conventional endoscopes. In addition, the endoscope of the present invention required 0.5 lbs. of force to push it through a 2-inch U-shaped bend where a conventional endoscope could not pass through such a tight bend. Therefore, the present invention allows colonoscopes to be made inexpensively and lightweight so that they are more comfortable for the patient due to their lower coefficient of friction and better trackability.

In addition to performing colonoscopies, the endoscopic imaging system of the present invention is also useful with a variety of surgical devices including: cannulas, guidewires, sphincterotomes, stone retrieval balloons, retrieval baskets, dilatation balloons, stents, cytology brushes, ligation devices, electrohemostasis devices, sclerotherapy needles, snares and biopsy forceps.

Cannulas are used with the endoscopic imaging system to cannulate the sphincter of Odi or papilla to gain access to the bile or pancreatic ducts. Guidewires can be delivered down the working channel of the endoscope and used as a rail to deliver a surgical device to an area of interest. Sphincterotomes are used to open the papilla in order to place a stent or remove a stone from a patient. Stone retrieval balloons are used along with a guidewire to pull a stone out of a bile duct. Retrieval baskets are also used to remove stones from a bile duct. Dilatation balloons are used to open up strictures in the gastrointestinal, urinary or pulmonary tracts. Stents are used to open up strictures in the GI, urinary or pulmonary tracts. Stents can be metal or plastic, self-expanding or mechanically expanded, and are normally delivered from the distal end of a catheter. Cytology brushes are used at the end of guidewires to collect cell samples. Ligation devices are used to ligate varices in the esophagus. Band ligators employ elastic bands to cinch varices. Electrohemostasis devices use electrical current to cauterize bleeding tissue in the GI tract. Sclerotherapy needles are used to inject coagulating or sealing solutions into varices. Snares are used to remove polyps from the GI tract, and biopsy forceps are used to collect tissue samples.

Examples of specific surgical procedures that can be treated with the endoscopic imaging system of the present invention include the treatment of gastroesophageal reflux disease (GERD) by the implantation of bulking agents, implants, fundoplication, tissue scarring, suturing, or replacement of valves or other techniques to aid in closure of the lower esophageal sphincter (LES).

Another example of a surgical procedure is the treatment of morbid obesity by deploying implants or performing reduction surgery, gastric bypass and plication or creating tissue folds to help patients lose weight.

Endoscopic mucosal resection (EMR) involves the removal of sessile polyps or flat lesions by filling them with saline or the like to lift them prior to resection. The endoscope of the present invention can be used to deliver needles, snares and biopsy forceps useful in performing this procedure.

In addition, the endoscopic imaging system of the present invention can be used to perform full-thickness resection (FTRD) in which a portion of a GI tract wall is excised and the wounds healed with staplers or fasteners. Finally, the endoscopic imaging system of the present invention can be used to deliver sclerosing agents to kill tissues or drug delivery agents to treat maladies of internal body tissues.

While the preferred embodiment of the invention has been illustrated and described, it will be appreciated that various changes can be made therein without departing from the scope of the invention. For example, although some of the disclosed embodiments use the pull wires to compress the length of the endoscope, it will be appreciated that other mechanisms such as dedicated wires could be used. Alternatively, a spring can be used to bias the endoscope distally and wires used to compress the spring thereby shortening the length of the endoscope. Therefore, the scope of the invention is to be determined from the following claims and equivalents thereof.

The embodiments of the invention in which an exclusive property or privilege is claimed are defined as follows:

1. An articulation joint for use in a steerable medical device, comprising: a plurality of connectors, each connector including: a body portion defining a first lumen and having a planar end that is substantially planar in a transverse direction to a longitudinal axis of the body portion; an insert portion extending axially and radially away from the planar end of the body portion and defining a second lumen extending from the first lumen of the body portion; a slot extending through a middle and sides of the insertion portion; and a plurality of openings extending through the body portion and surrounding an outer surface of the first lumen; wherein the insert portion of a connector is configured to be inserted into a first lumen of an adjacent connector to couple the connector to the adjacent connector.

2. The articulation joint of claim 1, wherein the body portion completely surrounds the first lumen.

3. The articulation joint of claim 1, wherein the first lumen opens into the second lumen.

4. The articulation joint of claim 3, wherein the first lumen includes a diameter larger than a diameter of the second lumen.

5. The articulation joint of claim 4, wherein a cross-sectional shape of the first lumen is complementary with a cross-sectional shape of the insert portion.

6. The articulation joint of claim 1, further comprising a plurality of control members disposed in the plurality of openings of the plurality of connectors, wherein actuation of the plurality of control members is configured to articulate the articulation joint.

7. The articulation joint of claim 1, wherein the insert portion includes a diameter smaller than a diameter of the body portion.

8. The articulation joint of claim 7, wherein, when the insert portion is inserted into the first lumen of the adjacent connector, the body portion surrounds the outer surface of the insert portion.

9. The articulation joint of claim 8, wherein the first lumens of adjacent connectors are in flow communication with each other.

10. The articulation joint of claim 1, wherein each opening extends axially through the body portion from a first end of the body portion to a second end of the body portion opposite the first end, and each opening does not extend through the insert portion.

11. An articulation joint for a medical device, comprising: a plurality of connectors, each connector including:
a body portion defining a first lumen and having a planar end that is substantially planar in a transverse direction to a longitudinal axis of the body portion;
an insert portion extending axially and radially away from the planar end of the body portion and defining a second lumen extending from the first lumen of the body portion;
a slot extending through a middle and sides of the insertion portion; and
a plurality of openings axially extending through a wall of the body portion and positioned around the first lumen;
wherein the insert portion of a connector is configured to be inserted into a first lumen of an adjacent connector to couple the connector to the adjacent connector.

12. The articulation joint of claim 11, wherein the first lumen opens into the second lumen.

13. The articulation joint of claim 12, wherein the first lumen includes a diameter larger than a diameter of the insert portion.

14. The articulation joint of claim 13, wherein a cross-sectional shape of the first lumen is complementary with a cross-sectional shape of the insert portion.

15. An articulation joint of claim 11, wherein the body portion completely surrounds the first lumen;
wherein the first lumen opens into the second lumen, the first lumen includes a diameter larger than a diameter of the second lumen, a cross-sectional shape of the first lumen is complementary with a cross-sectional shape of the insert portion, and the insert portion includes a diameter smaller than a diameter of the body portion;

wherein each opening extends axially through the body portion from a first end of the body portion to a second end of the body portion;

wherein, when the insert portion is inserted into the first lumen of the adjacent connector, the body portion surrounds the outer surface of the insert portion; and wherein the first lumens of adjacent connectors are in flow communication with each other.

16. The articulation joint of claim 15, wherein at least one opening of each connector extends through the body portion of the connector, and wherein the insert portion of the connector is configured to move relative to the first lumen of the adjacent connector.

17. The articulation joint of claim 15, further comprising a plurality of control members disposed in the plurality of openings of the plurality of connectors, wherein actuation of the plurality of control members is configured to articulate the articulation joint.

* * * * *